(12) United States Patent
Andrews et al.

(10) Patent No.: US 9,022,923 B2
(45) Date of Patent: *May 5, 2015

(54) IMPLANTABLE INJECTION PORT WITH TISSUE IN-GROWTH PROMOTER

(75) Inventors: James C. Andrews, Denver, CO (US); Amy L. Marcotte, Mason, OH (US); Sarah A. Noschang, Mason, OH (US); Eric W. Thompson, Pleasant Plain, OH (US); Scott A. Woodruff, Cincinnati, OH (US); Michael J. Vendely, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 322 days.

This patent is subject to a terminal disclaimer.

(21) Appl. No.: 12/946,913

(22) Filed: Nov. 16, 2010

(65) Prior Publication Data

US 2012/0123342 A1    May 17, 2012

(51) Int. Cl.
*A61F 2/00*      (2006.01)
*A61F 13/00*     (2006.01)
*A61M 39/02*     (2006.01)
*A61M 5/142*     (2006.01)

(52) U.S. Cl.
CPC ....... *A61M 39/0208* (2013.01); *A61M 5/14276* (2013.01)

(58) Field of Classification Search
CPC ..... A61F 5/005; A61F 5/0053; A61F 5/0056; A61F 5/0059; A61F 5/0063; A61M 39/0208; A61M 2039/0211; A61M 2039/0214; A61M 2039/022; A61M 2039/0223; A61M 2039/0226; A61M 2039/0238; A61M 2039/0244

USPC ................. 600/37; 604/175, 288.01–288.04; 606/151

See application file for complete search history.

(56) References Cited

U.S. PATENT DOCUMENTS

| | | | |
|---|---|---|---|
| 5,090,954 A * | 2/1992 | Geary | 604/29 |
| 5,906,596 A * | 5/1999 | Tallarida | 604/175 |
| 6,067,991 A | 5/2000 | Forsell | |
| 6,461,292 B1 | 10/2002 | Forsell | |
| 6,470,892 B1 | 10/2002 | Forsell | |
| 7,416,528 B2 | 8/2008 | Crawford et al. | |
| 7,442,165 B2 | 10/2008 | Forsell | |
| 7,621,863 B2 | 11/2009 | Forsell | |
| 7,699,770 B2 | 4/2010 | Hassler, Jr. et al. | |
| 7,762,998 B2 | 7/2010 | Birk et al. | |
| 7,775,215 B2 | 8/2010 | Hassler, Jr. et al. | |

(Continued)

FOREIGN PATENT DOCUMENTS

EP    1704891       9/2006
WO   WO 2010/096589   8/2010

OTHER PUBLICATIONS

International Search Report dated Mar. 12, 2012 for Application No. PCT/US2011/060895.

*Primary Examiner* — Jacqueline Cheng
*Assistant Examiner* — Eileen Hyde

(57) ABSTRACT

A surgically implantable injection port has one or more tissue in-growth promoting surfaces. The injection port includes a housing, a fluid reservoir defined in part by the housing, a needle penetrable septum, and a tissue in-growth promoting surface integrally provided on an exterior surface of the port. The tissue in-growth promoting surface may be provided by surgical mesh or a textured surface on the injection port. The injection port may be used as part of a gastric band system or some other type of system.

6 Claims, 19 Drawing Sheets

(56) References Cited

U.S. PATENT DOCUMENTS

| | | |
|---|---|---|
| 7,850,660 B2 | 12/2010 | Uth et al. |
| 2004/0068233 A1 | 4/2004 | DiMatteo |
| 2005/0192608 A1* | 9/2005 | Moreno et al. ............... 606/167 |
| 2006/0199997 A1 | 9/2006 | Hassler et al. |
| 2006/0217673 A1* | 9/2006 | Schulze et al. ........... 604/288.02 |
| 2006/0264898 A1* | 11/2006 | Beasley et al. ............... 604/506 |
| 2007/0112360 A1* | 5/2007 | De Deyne et al. ............ 606/151 |
| 2007/0198039 A1* | 8/2007 | Jones et al. .................. 606/151 |
| 2008/0269552 A1* | 10/2008 | Montpetit et al. .............. 600/37 |
| 2010/0274195 A1 | 10/2010 | Eichers et al. |
| 2011/0054407 A1* | 3/2011 | Olroyd et al. ................. 604/174 |
| 2011/0118677 A1* | 5/2011 | Wiley et al. ............. 604/288.01 |
| 2011/0196195 A1* | 8/2011 | Raven et al. .................... 600/37 |
| 2011/0306827 A1* | 12/2011 | Chitre et al. .................... 600/37 |

* cited by examiner

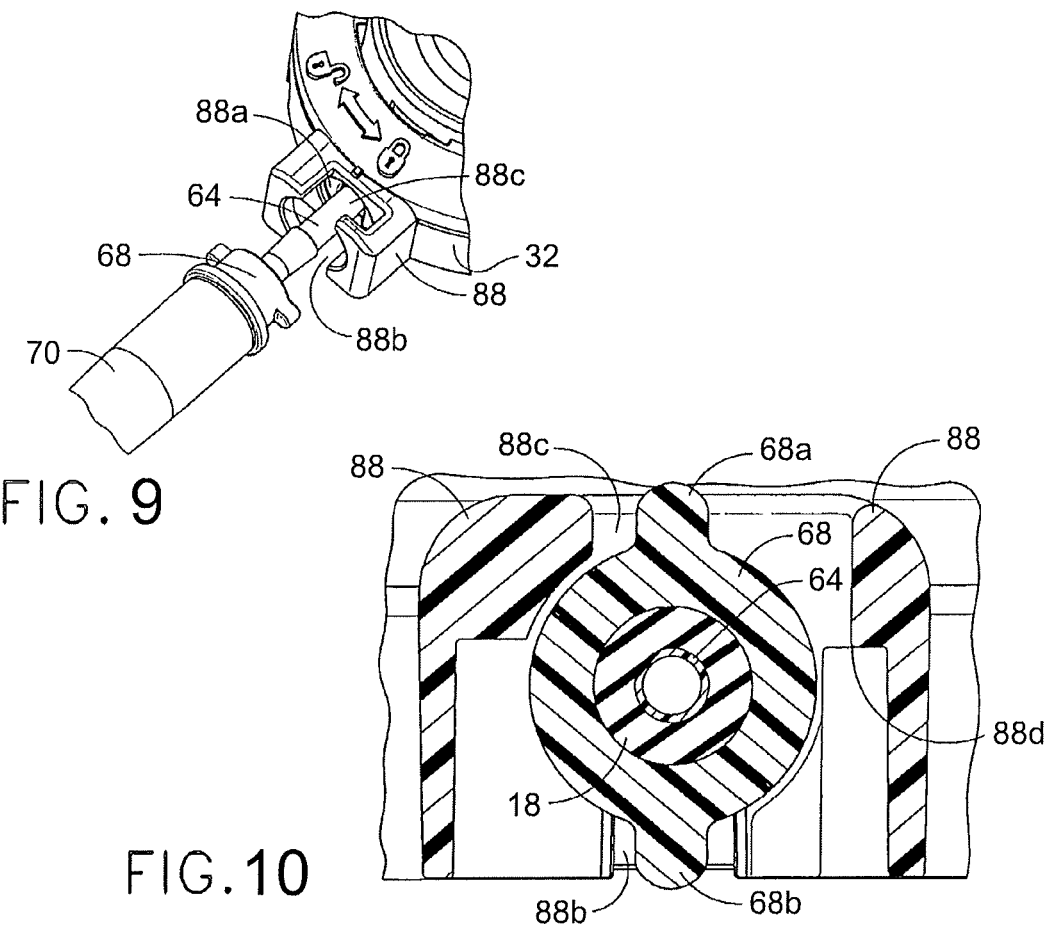
FIG. 9
FIG. 10
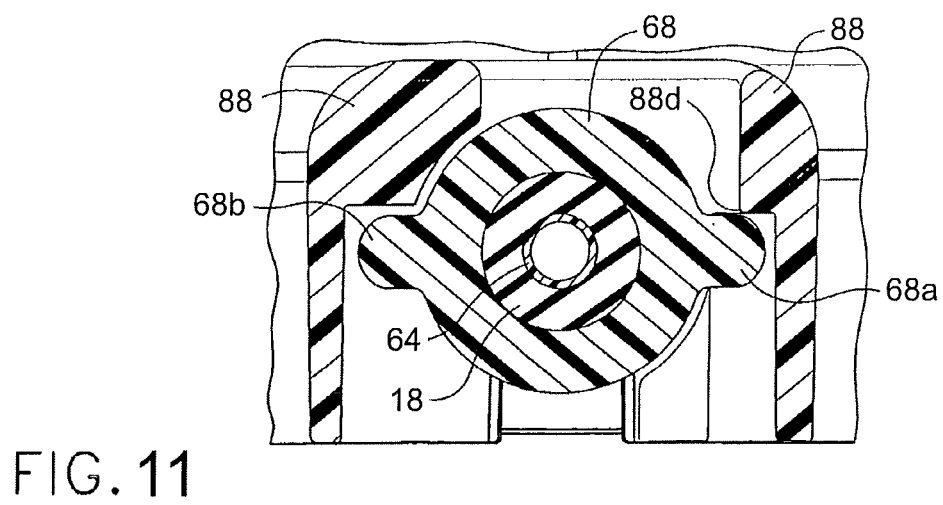
FIG. 11

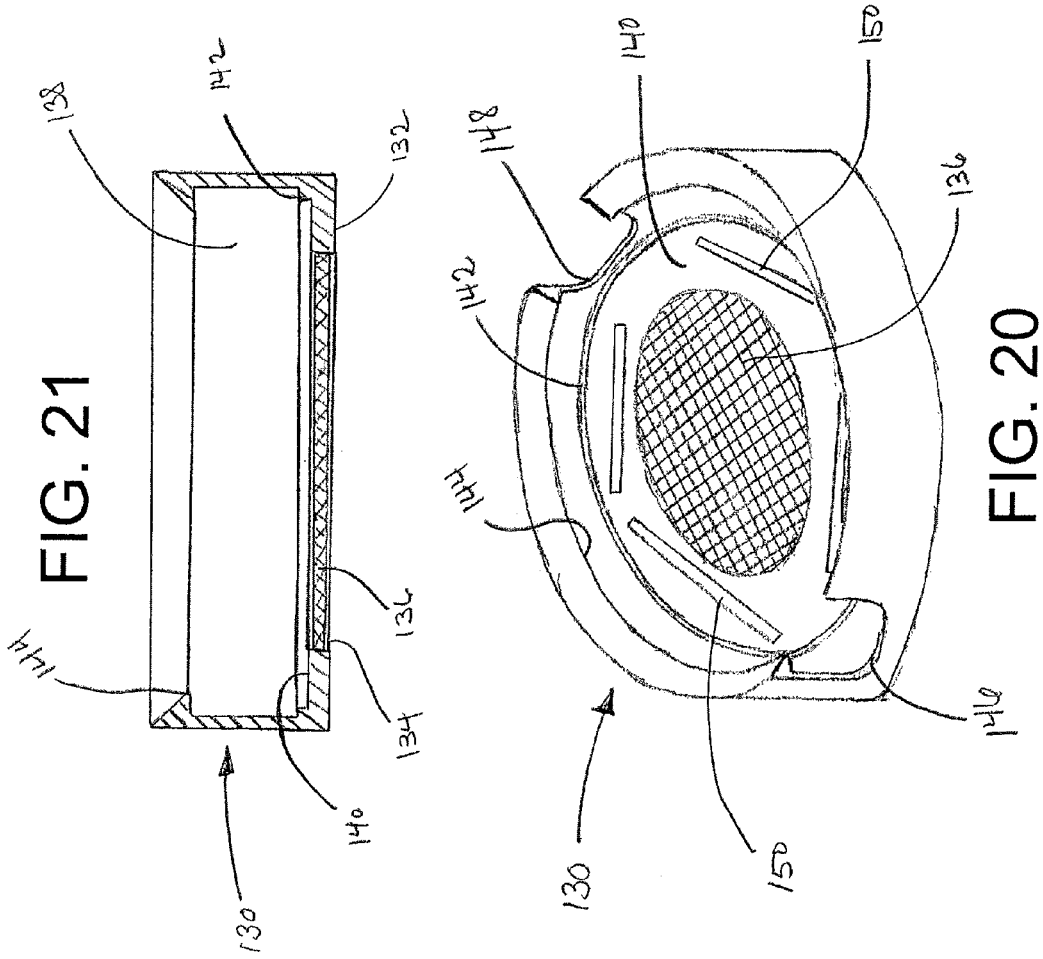

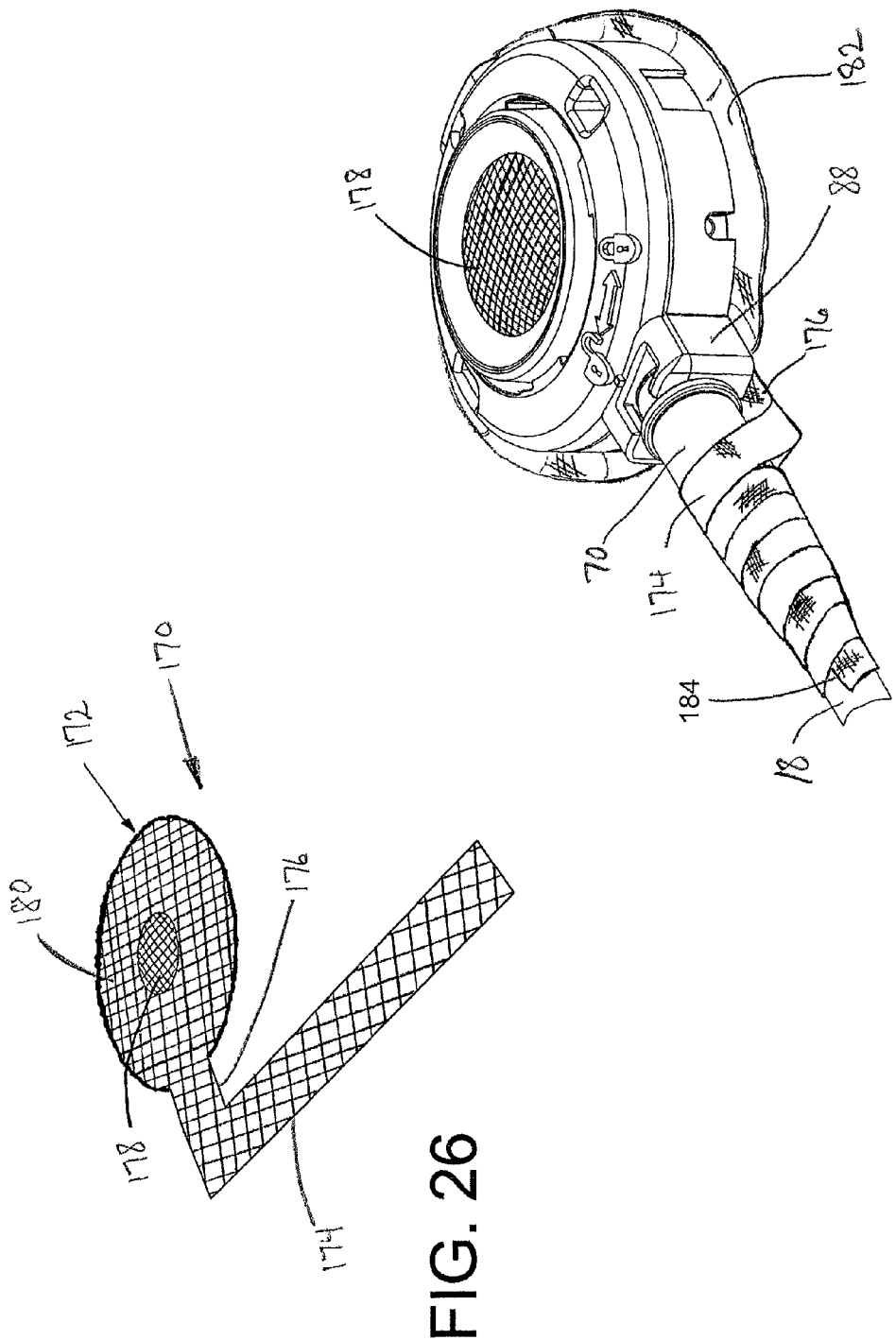

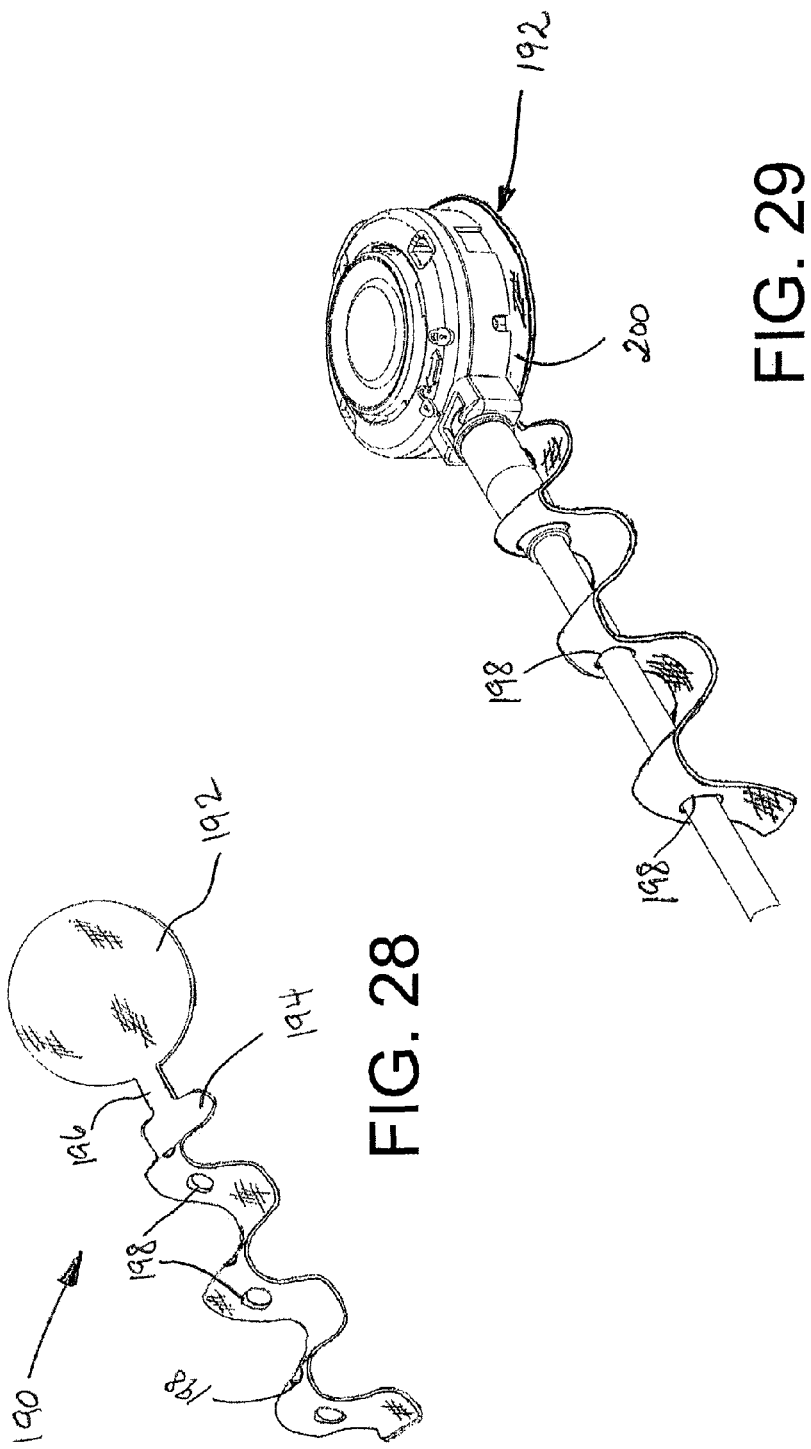

IMPLANTABLE INJECTION PORT WITH TISSUE IN-GROWTH PROMOTER

BACKGROUND

Implantable medical devices may be implanted in a patient to perform a therapeutic function for that patient. Non-limiting examples of such devices include pace makers, injection ports (such as infusion ports as well as ports used with gastric band systems), and gastric pacing devices. Such implants may need to be attached, perhaps subcutaneously, in an appropriate place in order to function properly. It may be desirable that the procedure to implant such devices be quick, easy and efficient.

Injection ports may be placed beneath the skin of a body for injecting fluids into the body, such as for infusing medication, blood draws, and many other applications, including adjustable gastric band systems. Gastric band systems are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Another example of such an adjustable gastric band is disclosed in U.S. Pat. No. 6,067,991, entitled "Mechanical Food Intake Restriction Device," issued May 30, 2000, the disclosure of which is incorporated by reference herein.

To the extent that an adjustable gastric band system includes an injection port configured to receive the needle of a syringe assembly in order to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled "System and Method for Determining Implanted Device Positioning and Obtaining Pressure Data" published Sep. 21, 2006, and issued Aug. 17, 2010 as U.S. Pat. No. 7,775,215, the disclosure of which is incorporated by reference herein.

Those of ordinary skill in the art will appreciate that it may be advantageous in certain circumstances to sense pressure, strain, and/or other parameters associated with operation of a gastric band device. In some settings, it may be desirable to obtain data indicative of the pressure of fluid in a gastric band. Various examples of methods and devices for obtaining pressure data and other types of data are disclosed in U.S. Pub. No. 2006/0189888, entitled "Device for Non-Invasive Measurement of Fluid Pressure in an Adjustable Restriction Device," published Aug. 24, 2006, and issued Apr. 20, 2010 as U.S. Pat. No. 7,699,770, the disclosure of which is incorporated by reference herein. Additional examples of methods and devices for obtaining pressure data and other types of data are disclosed in U.S. Pub. No. 2006/0199997, entitled "Monitoring of a Food Intake Restriction Device," published Sep. 7, 2006, and issued Sep. 13, 2011 as U.S. Pat. No. 8,016,745, the disclosure of which is incorporated by reference herein. Such parameter data may be obtained before, during, and/or after adjustment of a gastric band, and may be useful for adjustment, diagnostic, monitoring, or other purposes, and may also be obtained with respect to a mechanically actuated gastric band. In settings where a fluid-filled gastric band is used, pressure data may be used to determine whether the amount of fluid in the gastric band needs to be adjusted; and/or for other purposes.

While a variety of injection ports and gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 9 depicts an enlarged, fragmentary, exploded perspective view of the fitting and locking connector of the injection port of FIG. 5;

FIG. 10 depicts an enlarged, fragmentary partial cross-section view of the locking connector of FIG. 9 assembled to the fitting the septum retainer but not locked in place;

FIG. 11 depicts an enlarged, fragmentary partial cross-section view similar to FIG. 10 showing the locking connector locked in place;

FIG. 20 depicts a perspective view of an exemplary frame attachable to an injection port, with the frame including a tissue in-growth promoting surface;

FIG. 21 depicts a cross-sectional view of the frame depicted in FIG. 20;

FIG. 26 depicts a perspective view of an exemplary surgical mesh structure configure for use with an injection port;

FIG. 27 depicts a perspective view of the surgical mesh structure of FIG. 26 mounted on an exemplary injection port and associated fluid conduit;

FIG. 28 depicts a perspective view of an exemplary alternative surgical mesh structure configured for use with an injection port;

FIG. 29 depicts a perspective view of the surgical mesh structure of FIG. 28 mounted to an exemplary injection port and associated fluid conduit.

Figure 1:
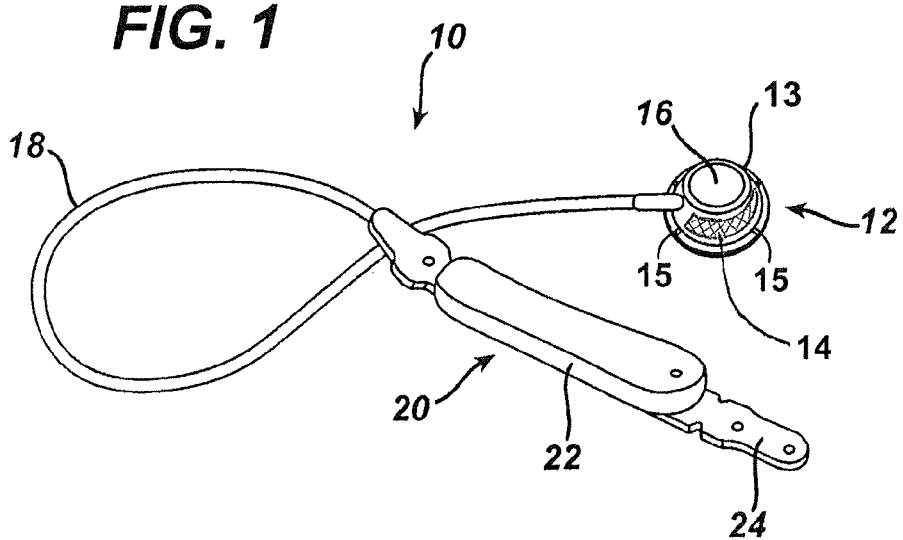
FIG. 1 depicts a perspective view of an implantable portion of an exemplary gastric band system, including an injection port having a tissue in-growth promoting surface.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various examples of ports having tissue in-growth promoting surfaces and/or features are depicted and described as being part of a gastric band system, the tissue in-growth surfaces and features may be employed with other types of implantable medical ports or other medical devices. Accordingly, the drawings and descriptions should be regarded as illustrative in nature and not restrictive.

I. Exemplary Gastric Band System

FIGS. 1-4 illustrate an exemplary gastric band system (10). As shown, gastric band system (10) comprises an injection port (12), a gastric band (20), and a flexible conduit (or catheter) (18). Injection port (12) of the present example comprises a port housing (13), a needle penetrable septum (16) and a fluid reservoir (not shown in FIGS. 1-4) located beneath septum (16). Catheter (18) (e.g., a flexible polymeric tube) is attached to port housing (13) in fluid communication with the fluid reservoir therein. A needle may pierce septum (16) to reach the reservoir and add or withdraw fluid (e.g., saline, etc.), as described in greater detail below.

Port housing (13) may comprise a unitary structure (e.g., a one piece housing insert molded about septum (16), etc.). Alternatively, port housing (13) may be assembled from two or more mating components such as a port body that at least partially receives a port base therein (as further described herein). Port housing (13) may be formed of titanium, plastic, or any other suitable material or combination of materials. Septum (16) may be formed of silicone or any other suitable material or combination of materials.

Injection port (12) of the present example also includes at least one tissue in-growth promoting surface (14), which extends about at least a portion of an outer surface of port housing (13). In some versions, and as further described herein, tissue in-growth promoting surface (14) comprises surgical mesh (e.g., polypropylene mesh) integrally provided on (e.g. bonded to) or adjacent to an outer surface of port housing (13), such as a peripheral sidewall of port housing (13) (as shown) and/or a bottom surface of port housing (13).

Injection port (12) may be subcutaneously secured over a patient's sternum, to the patient's abdominal fascia, or in any other suitable location. In the present example, port (12) may be sutured in place using the suture apertures (15) located about the periphery of port housing (13). It will be understood that the configuration of port (12) is merely exemplary of some possible versions. One or more tissue in-growth promoting surfaces may be provided on one or more portions of any of a variety of injection ports, including ports configured to be sutured in place as well as ports configured to be held in place using one ore fasteners. By way of example only, an injection port having one or more tissue in-growth promoting surfaces (e.g., mesh integrally provided on the port) may be configured and operable in accordance with the teachings of U.S. Pat. No. 7,762,998, entitled "Implantable Device Fastening System and Methods of Use," issued Jul. 27, 2010, the disclosure of which is incorporated by reference herein. In some other versions, and as further described herein, injection port (12) may be configured and operable in accordance with the teachings of U.S. Pub. No. 2005/0283118, entitled "Implantable Medical Device with Simultaneous Attachment Mechanism and Method," published Dec. 22, 2005, and issued Dec. 14, 2010 as U.S. Pat. No. 7,850,660, the disclosure of which is incorporated by reference herein. Alternatively, injection port (12) may have any other suitable configuration and/or operability.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). Catheter (18) may be formed of silicone or any other suitable material or combination of materials. In the present example, catheter (18), bladder (22), and injection port (12) form a closed fluid circuit. Accordingly, a needle that is inserted through septum (16) into the underlying reservoir may be used to add fluid to or withdraw fluid from inflatable bladder (22) in order to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
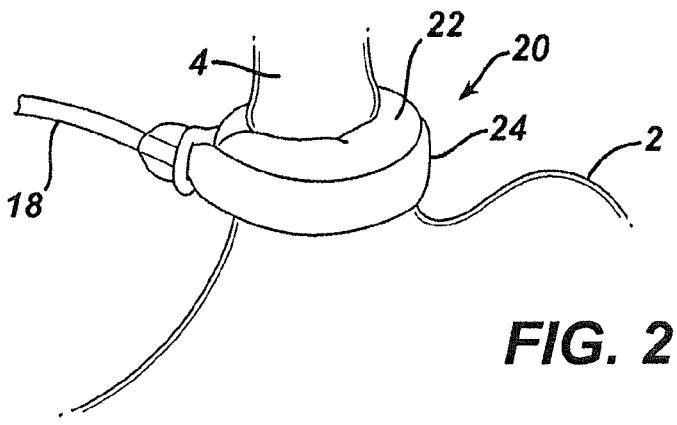
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastro-esophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction, or increased by withdrawing fluid from bladder (22) to reduce the degree of restriction.

Figure 3:
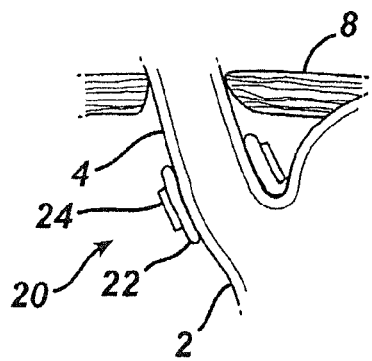
FIG. 3 depicts a cross-sectional view of the gastric band of FIG. 1, showing the band positioned around the gastro-esophageal junction of a patient in a deflated configuration.
Figure 4:
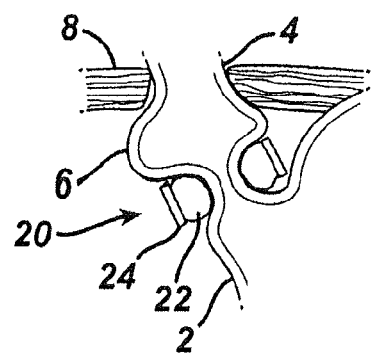
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encompasses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

As mentioned previously, injection port (12) may be subcutaneously secured over a patient's sternum, to the patient's abdominal fascia, or in any other suitable location. While injection port (12) may be secured in place by integral fasteners, sutures, or other fastening members (or any combination of one or more of the foregoing), injection port (12) may become dislodged or otherwise displaced from its original location after implantation in some instances. In addition, injection port (12) may be mobile, making it difficult to insert a needle through the septum (16) in order to add or remove fluid. Also, catheter (18) may become detached from injection port (12), potentially allowing fluid to leak from bladder (22) and/or the fluid reservoir within injection port (12), or at least cutting off fluid communication from injection port (12) to bladder (22).

In order to help reduce the likelihood of (if not prevent) dislodgement or displacement of injection port (12), limit the mobility of injection port (12), and/or prevent detachment of catheter (18) from injection port (12), one of more tissue in-growth promoting surfaces may be provided on, or associated with, injection port (12) and/or catheter (18). In the example shown in FIG. 1, a tissue in-growth promoting surface comprising surgical mesh (14) is integrally provided on an outer surface of port housing (13). As used herein, the phrase "integrally provided on" simply means that the surgical mesh generally cannot be removed from the port without damaging the mesh or, in some versions, disassembling the injection port (e.g., in the case of surgical mesh mounted within the port, etc.). Following implantation of port (12), tissue surrounding port (12) may grow into surgical mesh (14) (e.g., into the openings between adjacent fibers and around the fibers of the mesh, etc.). Such tissue in-growth may assist in retaining port (12) in place and limiting the mobility of port (12).

Surgical mesh (14), as well as the surgical mesh used in other examples described herein, may be formed from any biologically-compatible, porous medical textile, and/or open-matrix material suitable for implantation in a patient. Such materials may be similar to those used for reinforcing tissue defects, such as mesh slings used for hernia repair. The surgical mesh may comprise, for example, synthetic and/or naturally-derived filaments or wires that are woven, knitted, molded, or otherwise formed into a porous mesh or open-matrix structure that acts as a lattice allowing tissue in-growth between and/or around the filaments or wires. Suitable surgical mesh materials may include, for example, knitted polypropylene mesh fabrics such as those available from Ethicon, Inc. under the Prolene, Vicryl and Panacryl trademarks. Other suitable materials include, for example, a mesh or open-matrix structure formed of stainless steel, titanium, or other metal filaments or wires suitable for implantation. It should also be noted that the surgical mesh may be manufactured from two or more different materials, such as mesh having both non-absorbable and absorbable filaments for further promoting tissue in-growth. Various other suitable materials, combinations of materials, and configurations that may be used for a surgical mesh will be apparent to those of ordinary skill in the art in view of the teachings herein.

II. Injection Port with Tissue in-Growth Promoting Feature

A. Tissue in-Growth Promoting Material Bonded to One or More Port Surfaces

FIGS. 5-11 show an alternative injection port (26) suitable for use, for example, as part of a gastric band system. Injection port (26) includes one example of a tissue in-growth promoting surface integrally provided on the injection port. Although the tissue in-growth promoting features are illustrated in the figures as being embodied in or associated with injection port (26), the tissue in-growth promoting features described herein may be used with any implantable medical device for which it is suited, including by way of example only pacemakers, other types of implantable injection ports (such as vascular access ports), and gastric pacing devices. It should be noted that injection port (26) is similar in construction to the port depicted and described in U.S. Pub. No. 2005/0283118, issued as U.S. Pat. No. 7,850,660, and additional details concerning the construction and operation of port (26) may be provided in accordance with the teachings of U.S. Pub. No. 2005/0283118, issued as U.S. Pat. No. 7,850,660. Of course the tissue in-growth promoting features shown in FIGS. 5-11 may alternatively be provided on any other type of injection port suitable for implantation in a patient.

Injection port (26) includes septum (28), as well as a port housing comprising port base (30), port body (32), and actuator (36). Port base (30) acts as a retainer for septum (28) and is configured to nest at least partially within port body (32) such that septum (28) is compressed between port base (30) and port body (32). As further described herein, a fluid reservoir (58) is defined by port base (30) beneath septum (28).

Figure 7:
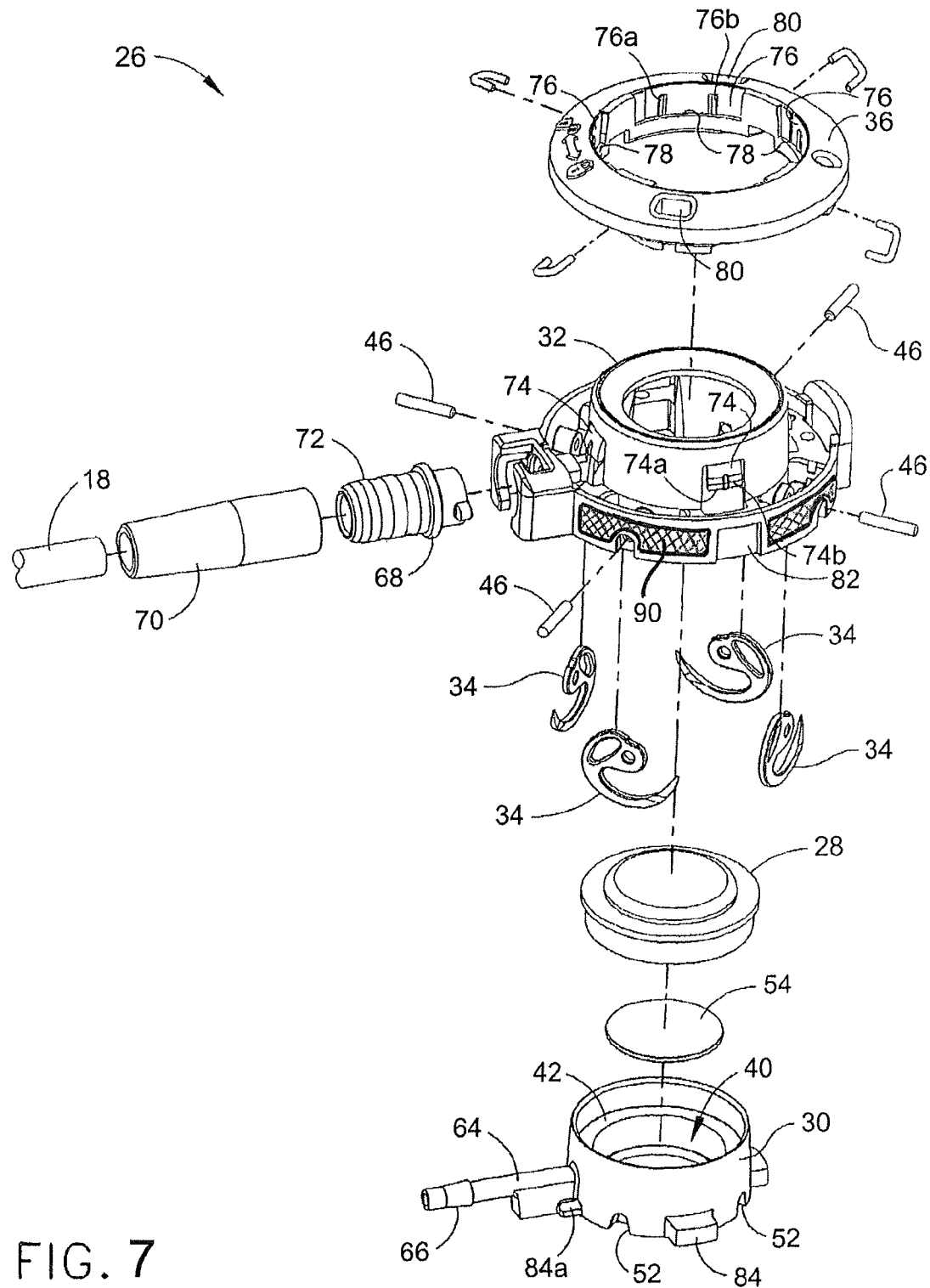
FIG. 7 depicts an exploded perspective view of the injection port of FIG. 5.
Figure 8:
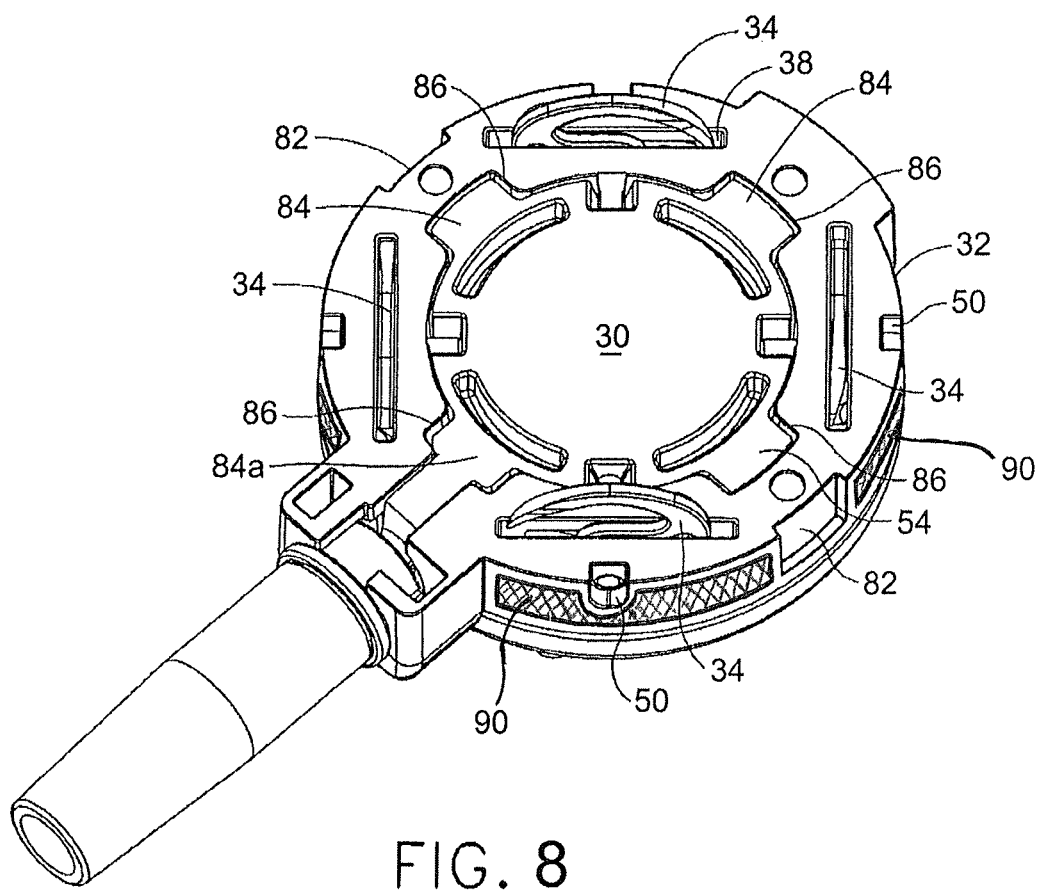
FIG. 8 depicts a perspective view of the bottom of the injection port of FIG. 5, showing the fasteners in the extended/fired position.

As best seen in FIGS. 7 and 8, injection port (26) also includes one or more fasteners (34) for securing injection port (26) subcutaneously within a patient. As further described in detail in U.S. Pub. No. 2005/0283118, issued as U.S. Pat. No.

7,850,660, rotation of actuator (36) with respect to port body (32) may be used to deploy the fasteners (34) so as to secure port (26) in place. Fasteners rotate within port body (32) so as to be deployed through slots in the bottom surface of port body (32), as shown in FIG. 8.

It will be understood that the construction of injection port (26) is merely exemplary of one possible version. For example, the injection port may be greatly simplified to include a port body (or housing) configured to retain a septum, and having a fluid reservoir (or chamber) located beneath the septum, and a catheter may be attached to the injection port in fluid communication with the fluid reservoir (e.g., similar in construction to port (12) in FIG. 1, etc.).

Figure 6:
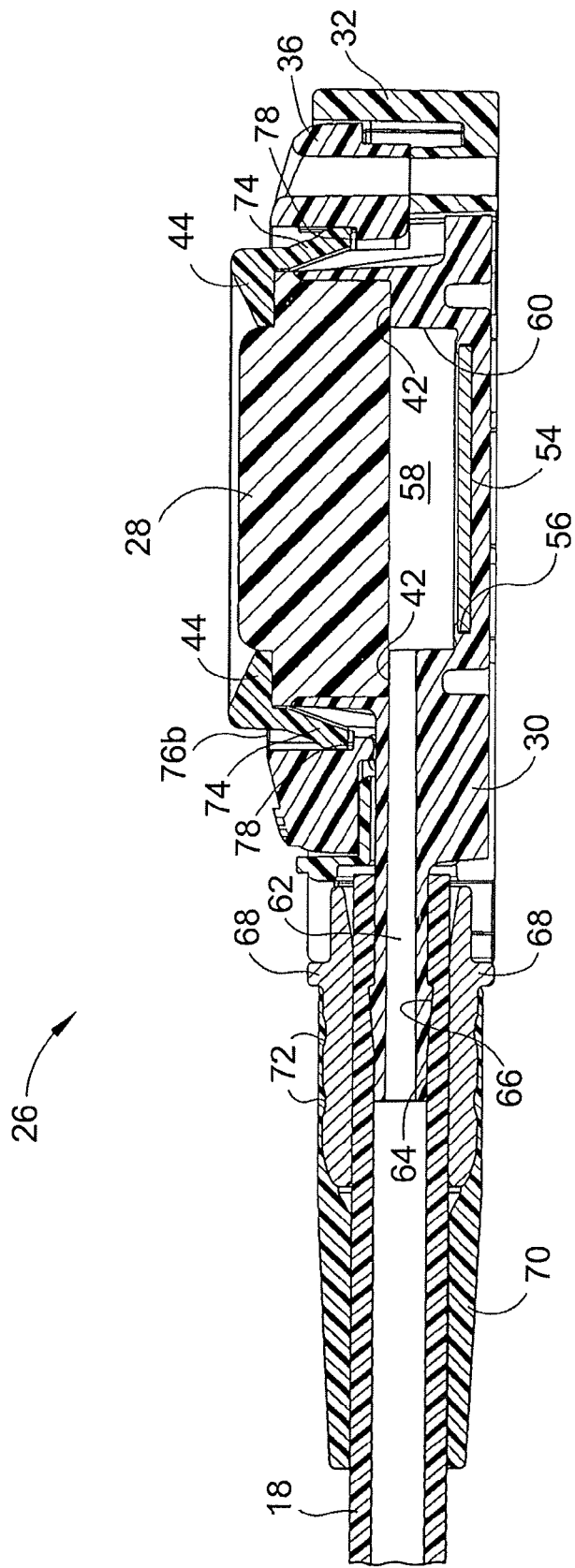
FIG. 6 depicts a side cross sectional view of the injection port of FIG. 5.

As seen in FIGS. 6 and 7, septum (28), which may be made of any suitable biocompatible material such as silicone, is disposed partially within internal cavity (40) of port base (30), adjacent annular flat (42). Port base (30), port body (32), and actuator (36) may be made of any suitable biocompatible material having sufficient stiffness and strength, such as polyether ether ketone (known as PEEK) or other plastic suitable for implantation in a patient. Fasteners (34) may be made of any suitable biocompatible material, such as stainless steel.

Port body (32) includes annular rim (44), which engages the upper surface of septum (28) about an annular portion. Port body (32) is retained to port base (30) by a plurality of pins (46), which are disposed through respective holes (48) formed in recesses (50) in port body (32) and which extend inwardly into respective recesses (52) formed about the bottom periphery of port base (30). Pins (46) may be made of any suitable biocompatible material, such as stainless steel. When port (26) is assembled as shown, septum (28) is sufficiently compressed between port base (30) and port body (32) so as to be adequately self-healing and thus maintain a fluid tight system under pressure even after multiple penetrations by a needle.

Plate (54) is disposed in recess (56) formed in the bottom of port base (30), underlying septum (28) and fluid reservoir (58). As seen in FIG. 6, plate (54) does not contact the sidewall (60) that defines the outer periphery of fluid reservoir (58). When a needle is inserted through septum (28) to introduce or withdraw fluid from fluid reservoir (58), such as in order to adjust the size of an adjustable gastric band, plate (54) will protect port base (30) from puncture and provide tactile feedback to the surgeon (through the needle) indicating that the needle has bottomed in reservoir (58). Plate (54) may be secured to port base (30) in any suitable manner.

Port base (30) includes passageway (62), in fluid communication with fluid reservoir (58), which is defined by tubular fitting (64) extending from the periphery adjacent the bottom of port base (30). Fluid conduit or catheter (18), which leads to adjustable gastric band (20), is connected to fitting (64), being compressingly urged against annular rib (66) by connector (68), which is disposed about catheter (18) and secured to port body (32). Sleeve (70) is disposed about catheter (18), secured to connector (68) by annular ribs (72). Sleeve (70) relieves strain on catheter (18), substantially preventing catheter (18) from kinking when loaded laterally.

Actuator (36) is rotatably secured to port body (32). Although in the present example actuator (36) is illustrated as an annular ring rotatably supported by port body (32), actuator (36) may be any suitable configuration and supported in any suitable manner to permit actuator (36) to function to move fasteners (34) between and including deployed and undeployed positions. As seen in FIG. 7, port body (32) includes a plurality of downwardly and outwardly extending tabs (74). In the present example, there are four equally spaced tabs (74). Actuator (36) includes an equal number of corresponding recesses (76), each having an arcuate bottom (78). To assemble actuator (36) to port body (32), recesses (76) are aligned with tabs (74), and actuator (36) is then pushed down, temporarily deflecting tabs (74) inwardly until tabs (74) reach recesses (76) and move outwardly to dispose lower edges (74a) in recesses (76) such that actuator (36) is retained thereby. The lengths of tabs (74) and depth of recesses (76) allow some axial end play between actuator (36) and port body (32) in the present example.

Actuator (36) may rotate generally about the central axis of port body (32). In the present example, actuator (36) may rotate through an angle of about 40 degrees, although any suitable angle may be used. Also in the present example, when actuator (36) is rotated in the deploying direction, fasteners (34) move to the deployed position shown in FIG. 8.

A detent system is formed by a pair of spaced apart raised detent ribs (76a, 76b) extending inwardly from the wall of each recess (76) and a corresponding raised rib (74b) extending outwardly from tab (74). The detent system assists in preventing actuator (36) from rotation and fasteners (34) from moving out of fully retracted or fully extended fired states under vibration or incidental loads, as described in U.S. Pub. 2005/0283118, issued as U.S. Pat. No. 7,850,660. To actuate the attachment mechanism, actuator (36) is rotated in a deploying direction, which in the present example is depicted as clockwise, though any other suitable direction configured to actuate an attachment mechanism may be used.

Actuator (36) further includes a plurality of spaced apart openings or slots (80), which may be engaged by any suitable instrument to transmit the necessary torque to rotate actuator (36) so as to extend fasteners (34) to the actuated position shown in FIG. 8. Slots (80) may be configured to be engaged by commercially available instruments, rectangular in the embodiment depicted, or by a dedicated applier such as that shown and described in U.S. Pub. No. 2005/0283118, issued as U.S. Pat. No. 7,850,660. Port body (32) of the present example includes a plurality of recesses (82) disposed about its lower periphery that are configured to cooperate with the dedicated applier, as further described in U.S. Pub. 2005/0283118, issued as U.S. Pat. No. 7,850,660.

Referring to FIG. 8, port base (30) includes a plurality of locating tabs (84) extending outwardly from adjacent the bottom periphery of port base (30). Locating tab (84a) may be integral with fitting (64). Port base (30) is inserted into the open bottom end of port body (32) such that tabs (84 and 84a) are located in respective complementarily shaped recesses (86) formed in the inner surface of port body (32), thus aligning port base (30) properly within port body (32). As further described in U.S. Pub. No. 2005/0283118, issued as U.S. Pat. No. 7,850,660, one or more apertures extending through actuator (36) and port body (32) may be provided, and these apertures may be used by the surgeon to suture injection port (26) subcutaneously in a patient, particularly if the integral attachment mechanism (e.g., fasteners (34)) is not used.

FIGS. 9-11 illustrate the locking connection between connector (68) and port body (32). FIG. 9 is an exploded perspective view showing fitting (64) partially surrounded by extension (88). FIG. 10 shows extension (88) in cross-section, with connector (68) generally disposed about fitting (64) and catheter (18) aligned in circumferential slot (88c) of extension (88). Connector (68) includes a pair of tabs (68a, 68b) extending outwardly therefrom. To assemble, connector (68) is guided along catheter (18) and fitting (64), with tabs (68a, 68b) aligned with openings (88a, 88b) of extension (88). With tabs (68a, 68b) aligned with circumferential slot (88c), connector (68) is rotated to lock it in place. During rotation, detent edge (88d) creates interference opposing the rotation of tab (68a), but is dimensioned to allow tab (68a) to be rotated past, to the locked position seen in FIG. 11.

Figure 5:
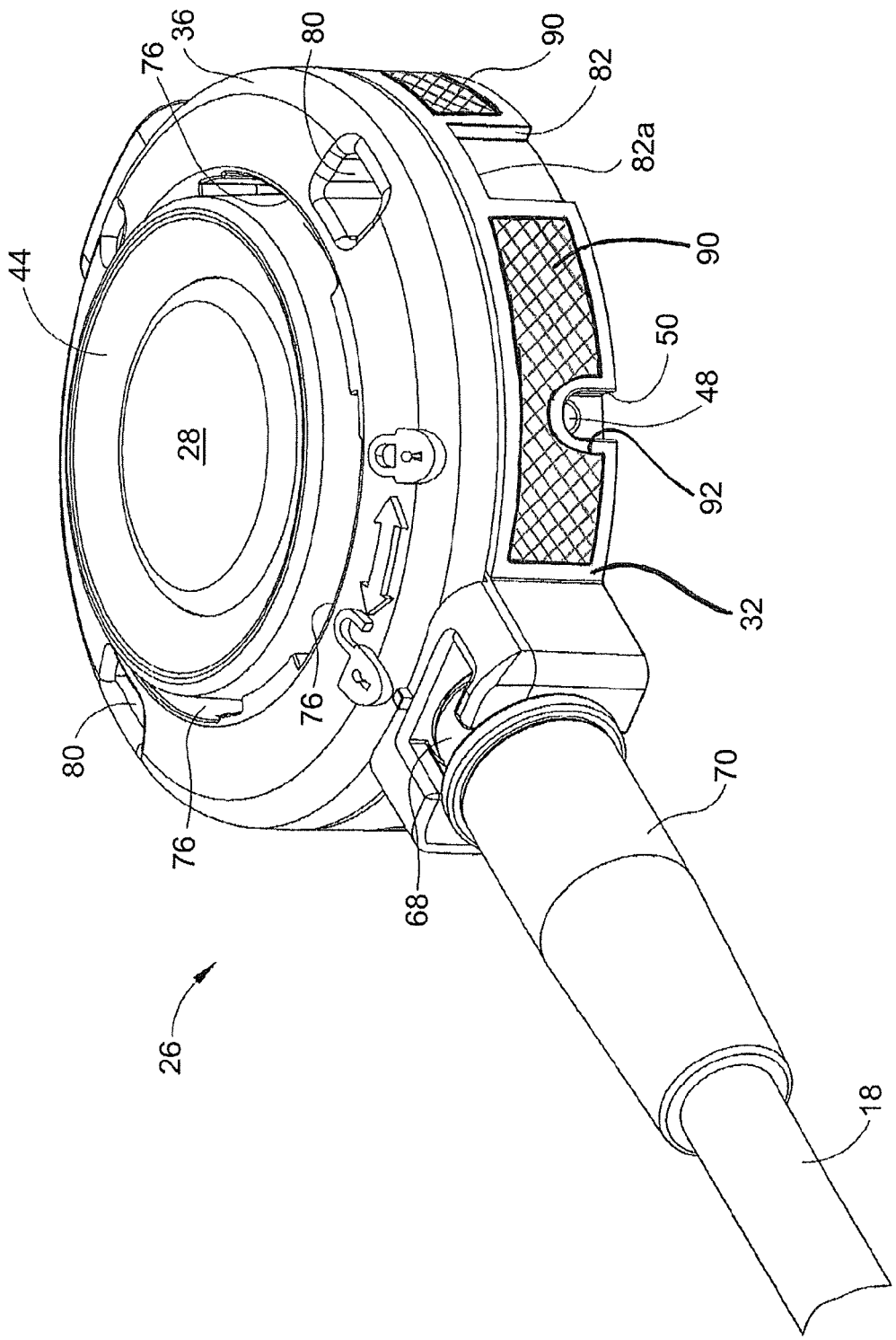
FIG. 5 depicts a perspective view of an exemplary alternative injection port having a tissue in-growth promoting surface.

While fasteners (34) and/or sutures may be used to subcutaneously secure port (26) in a patient, the example of port (26) shown in FIG. 5 also includes a plurality of tissue in-growth promoting surfaces. In some of the various examples shown and described further herein, one or more tissue in-growth promoting surfaces are provided on one or more exterior surfaces or portions of injection port (26). By way of example, the tissue in-growth promoting surface may comprise a tissue in-growth promoting material integrally provided on (e.g. bonded) to one or more regions of injection port (26). Alternatively, or in addition thereto, the tissue in-growth promoting surface may comprise one or more regions of injection port (26) that are textured or otherwise configured so as to promote tissue in-growth on and in such surface.

Suitable tissue in-growth promoting materials that may be affixed to one or more regions of injection port (26) so as to provide a tissue in-growth promoting surface may include, for example, biocompatible surgical mesh comprising a porous medical textile or open-matrix structure that acts as a lattice for tissue in-growth. The mesh may comprise, for example, synthetic and/or naturally-derived fibers, filaments, or wires that are woven, knitted, molded, or otherwise formed into a porous mesh or open-matrix structure that allows tissue growth between and/or around the fibers, filaments, or wires. Suitable polymeric materials for such mesh may include polypropylene mesh. Other suitable materials may include, for example, mesh made from stainless steel, titanium, and/or other metal filaments suitable for implantation. Any of a variety of mesh shapes and sizes may be employed. As further noted herein, surgical mesh of more than one mesh size and/or density may even be employed. In addition, the mesh may be made from two or more different types of fibers, filaments, or wires, such as mesh having both absorbable and non-absorbable filaments.

In the example shown in FIGS. 5-8, injection port (26) includes tissue in-growth promoting surfaces comprising biocompatible surgical mesh (90) affixed about a portion of the peripheral sidewall of port body (32). In the example shown, four sections of mesh (90) are provided. However, any number of sections of polypropylene mesh (90) may be provided on portions of the peripheral sidewall of port body (32) and/or on one or more other surfaces of port (26). Mesh (90) is configured so as not to interfere with the assembly or operation of injection port (26). Thus, in the example shown, each section of surgical mesh (90) comprises an arcuate strip with a cutout region (112) shaped and located so as to extend around the periphery of recess (50) (see FIG. 5). Of course it will be understood that any of a variety of shapes and sizes of mesh may be affixed to one or more outer surfaces of port (26).

Surgical mesh (e.g., polypropylene mesh) (90) may be permanently bonded to (i.e., integrally provided on) port body (32) in any of a variety of ways. For example, mesh (90) may be bonded to port body (32) using a bicopompatible adhesive (e.g., isocyanate or cyanoacrylate adhesive), heat staking, vibration welding, ultrasonic welding, hot/cold upset, mechanical attachments (e.g., interference fits, hooks, barbs, sutures, clamps, clips, etc.), and other ways known in the art. In the example shown, mesh (90) is bonded to the periphery of port body (32) using an adhesive.

Mesh (90) may be bonded to port (26) across substantially the entire under surface of mesh (90) (e.g., by a layer of adhesive between mesh (90) and port body (32), etc.). Alternatively, mesh (90) may be selectively bonded to port body (32) at one or more points or regions so as to provide one or more regions of mesh (90) that are not affixed to port (26). By way of example, mesh (90) may be bonded about its outer perimeter to port body (26) by heat staking such that the region of mesh (90) interior of its outer perimeter remains unattached to port body (32). Such unattached regions may allow additional tissue in-growth between mesh (90) and the wall of port body (32), particularly tissue in-growth around individual fibers of polypropylene mesh (90), thus further securing injection port (26) in place.

It will be understood that any number of sections of mesh (90) may be provided on injection port (26), attached to any of a variety of surfaces and locations. For example, mesh may be provided on the undersurface of port base (30), such as in the form of a circular mesh disc centrally located on the bottom surface of port base (30). The mesh disc may even extend over slots (38) in the bottom surface of port body (32), provided that the mesh is sufficiently thin so as to be penetrated by fasteners (34) when the fasteners (34) are deployed. Alternatively, or in addition thereto, mesh may be affixed about the upper surface of actuator (36), such as a plurality of arcuate strips arrayed about the upper surface of actuator (36) adjacent the outer circumference of septum (28).

Mesh or other tissue in-growth promoting material also may be affixed over top of septum (28), such as in the form of a round disc of mesh bonded or otherwise affixed to the outer surface of port base (30) or port body (32) adjacent septum (28) and/or affixed directly to the upper surface of septum (28) (e.g., using an adhesive). Provided that the mesh or other material is not too thick or dense, the mesh may be easily penetrated by a needle to allow the needle to be advanced through septum (28) in order to, for example, add or withdraw fluid from a gastric band system. Other suitable configurations and locations that may be used for mesh or any other suitable kind of mesh or similar structure will be apparent to those of ordinary skill in the art in view of the teachings herein.

B. Tissue in-Growth Promoting Material Bonded to Textured Port Surface

The area of injection port (26) to which the mesh (90) is attached may also be configured to further promote tissue in-growth. For example, the region(s) of the peripheral surface of port body (32) covered by mesh (90) may be textured so as to further promote tissue-in-growth. Such texturing may comprise, for example, a plurality of recesses, apertures, interconnected pores (e.g., a porous surface), ridges, protuberances (e.g., a roughened surface), trabeculae, or a combination of one or more of these features. Such features may provide areas where the mesh is spaced away from the surface of the injection port, thus allowing tissue to grow into the mesh and around the fibers of the mesh (e.g., tissue in-growth between portions of the mesh and the surface of the port to which the mesh is attached).

Figure 12:
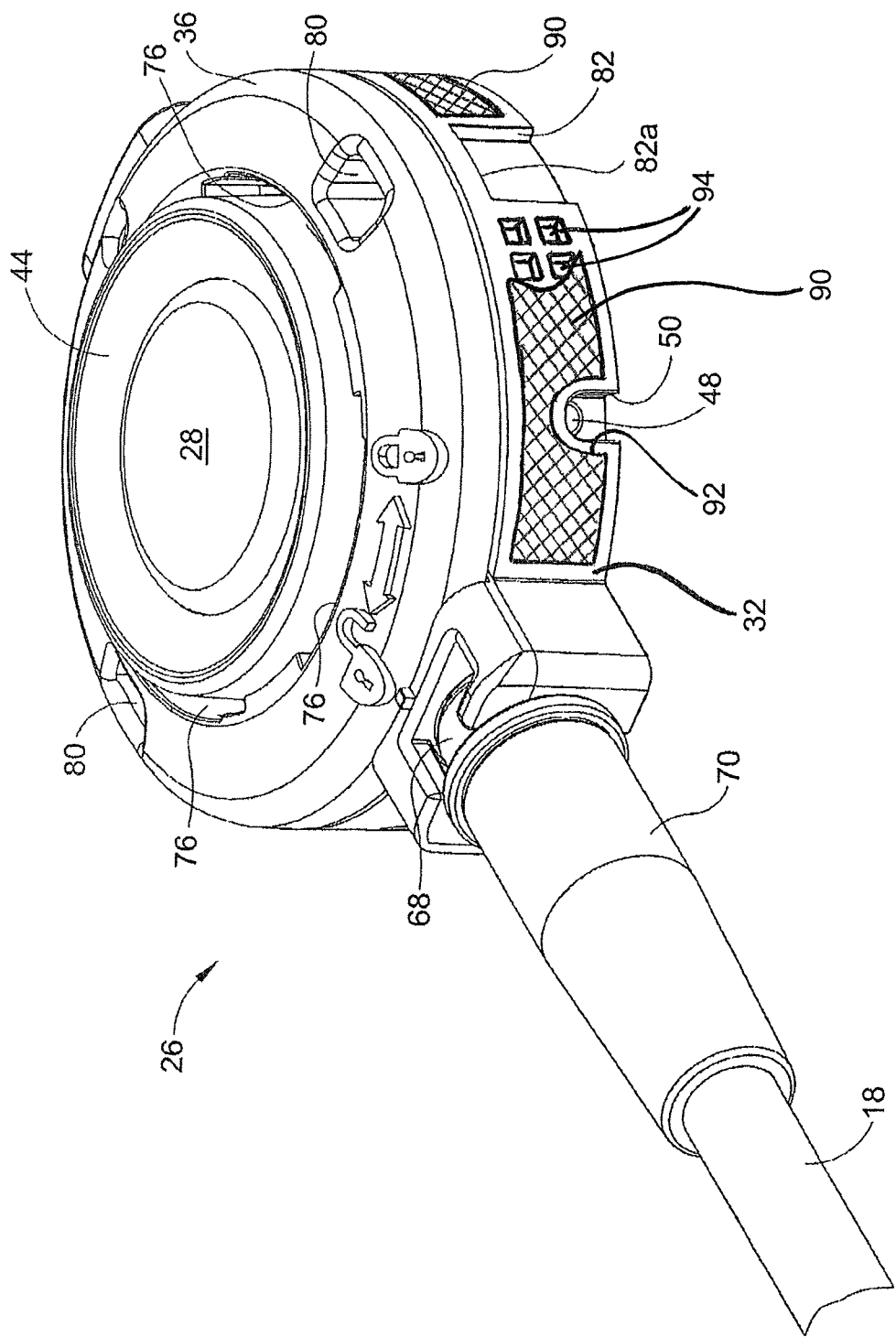
FIG. 12 depicts a perspective view of another exemplary alternative injection port having a tissue in-growth promoting surface.

By way of example, the region of the peripheral surface of the injection port covered by surgical mesh (or other tissue in-growth promoting material) may include one or more recesses that are covered by the mesh. In this manner, tissue is able to grow through the openings in the mesh, into the recess(es), around individual fibers of the mesh, and back out other openings in the mesh into adjacent tissue. An example of such a configuration is shown in FIG. 12, where mesh (90) has been partially cut-away to reveal an array of recesses (94) in the peripheral surface of port body (32). Recesses (94) are located so as to be covered by mesh (90). Such recesses (94) allow for tissue in-growth not only into recesses (94) but also around the individual fibers of mesh (90). Of course, recesses (94) are merely exemplary of one contemplated version.

Recesses of any of a variety of size, shape, number, arrangement, and location may be provided beneath mesh (90), adjacent to mesh, or elsewhere. For example, mesh (90) may be affixed to port (26) over a single recessed area such that mesh (90) is spaced away from the bottom of the recessed area.

C. Tissue in-Growth Promoting Surface(s) Integrally Provided on Injection Port

In place of bonding one or more tissue in-growth promoting materials to surfaces of injection port (26) (or in addition thereto), a tissue in-growth promoting surface may be integrally provided on one or more portions of injection port (26), such as by molding and the like. By way of example, a textured tissue in-growth promoting surface such as described previously may be formed (e.g., molded) on one or more surfaces of the injection port. As yet another alternative, one or more components of the injection port may be insert molded about one or more mesh layers or other porous layers. Some examples of such integral features will be discussed in greater detail below, while other examples will be apparent to those of ordinary skill in the art in view of the teachings herein.

1. Integral Mesh Layer on Port

Figure 13:
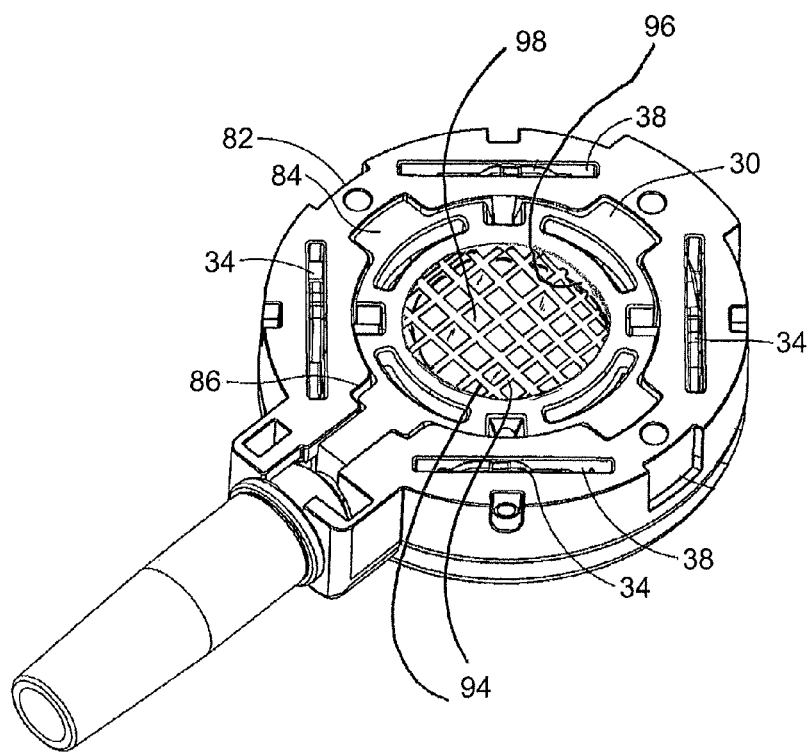
FIG. 13 depicts a perspective view of the bottom of yet another exemplary alternative injection port having a tissue in-growth promoting surface, showing the fasteners in the retracted/undeployed position.

In the example shown in FIG. 13, a mesh layer (94) is integrally provided adjacent the bottom surface of port base (30). In the example depicted, port base (30) is insert molded about mesh layer (94), which may comprise, for example, a surgical mesh of the type described previously. As another merely illustrative example, mesh layer (94) may comprise a substantially rigid plastic screen (e.g., PEEK, polysulfone, polyethylene, or other implant-grade material). In addition, mesh layer (94) may have openings of any of a variety of shapes, sizes and number. While the depicted example has rectangular openings, other shapes such as circular openings may be provided instead (or in addition thereto). Mesh layer (94) may be located within a circular cavity (96) formed in the bottom surface of port base (30). In the present example, the bottom surface (98) of cavity (96) is spaced away from mesh layer (94) so as to allow for greater tissue in-growth around the mesh. Of course such mesh layers may be integrally provided adjacent any of a variety of surfaces of injection port (26) (e.g., the sidewall of port body (32)), in a similar fashion or otherwise. In addition, any of a variety of other tissue in-growth promoting materials may be integrally provided adjacent one or more surfaces of the injection port (e.g., by insert molding and the like).

2. Textured Tissue in-Growth Promoting Surface

As yet another merely illustrative alternative, one or more surfaces of an injection port may be textured so as to promote tissue-in-growth. Such texturing may comprise, for example, a plurality of recesses, apertures, interconnected pores (e.g., a porous surface), ridges, protuberances (e.g., a roughened surface), trabeculae, or a combination of two or more of these features. Such texturing may provide areas for tissue in-growth, such as into recesses, apertures, or pores, and/or between ridges, other protuberances, or trabeculae, etc.

Figure 14:
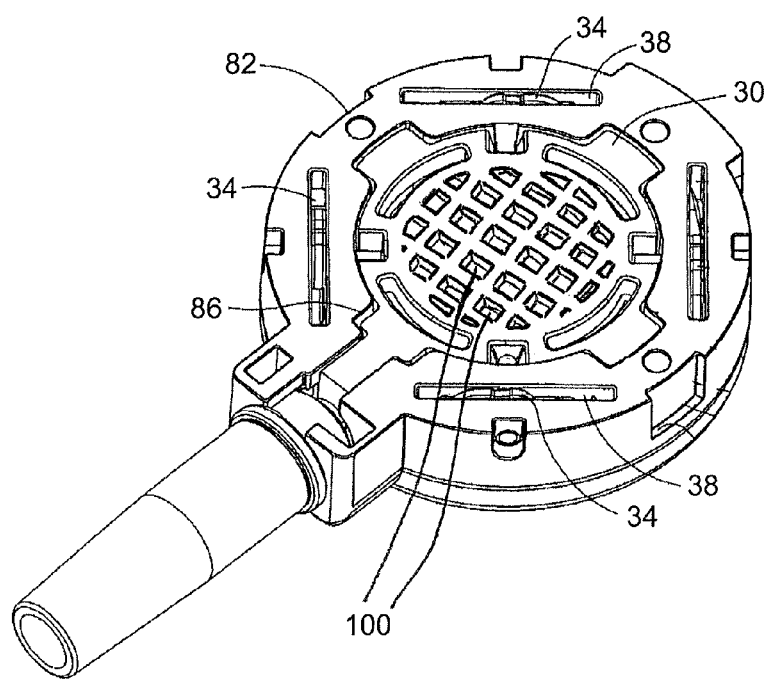
FIG. 14 depicts a perspective view of the bottom of another exemplary alternative injection port having a tissue in-growth promoting surface.

By way of example, and as shown in FIG. 14, a surface of the injection port is formed (e.g., molded) so as to include a plurality of recesses for promoting tissue growth into the recesses to assist in securing the port within a patient. In this particular embodiment, the bottom surface of port base (30) has been molded so as to include an array of recesses (100). The bottom surface of recesses (100) may also be textured (e.g., ridges or protuberances, etc.) to further promote tissue in-growth. One the injection port is implanted in a patient, tissue is able to grow into the recesses (100) in the bottom surface of port base (30). Of course, recesses of any of a variety of sizes, shapes, number, arrangements, and locations may be provided on one or more surfaces of the injection port.

D. Tissue in-Growth Promoting Material Mounted at Least Partially Within Injection Port As an alternative (or in addition) to bonding surgical mesh to one or more surfaces of the injection port or insert molding portions of the injection port around a mesh layer, a layer of biocompatible mesh (e.g., polypropylene mesh, etc.) may be mounted at least partially within the injection port such that one or more portions of the mesh are exposed for promoting tissue in-growth. One or more mesh layers may be mounted within the injection port, for example, by positioning at least a portion of the mesh between two port components that are secured to one another.

Figure 15:
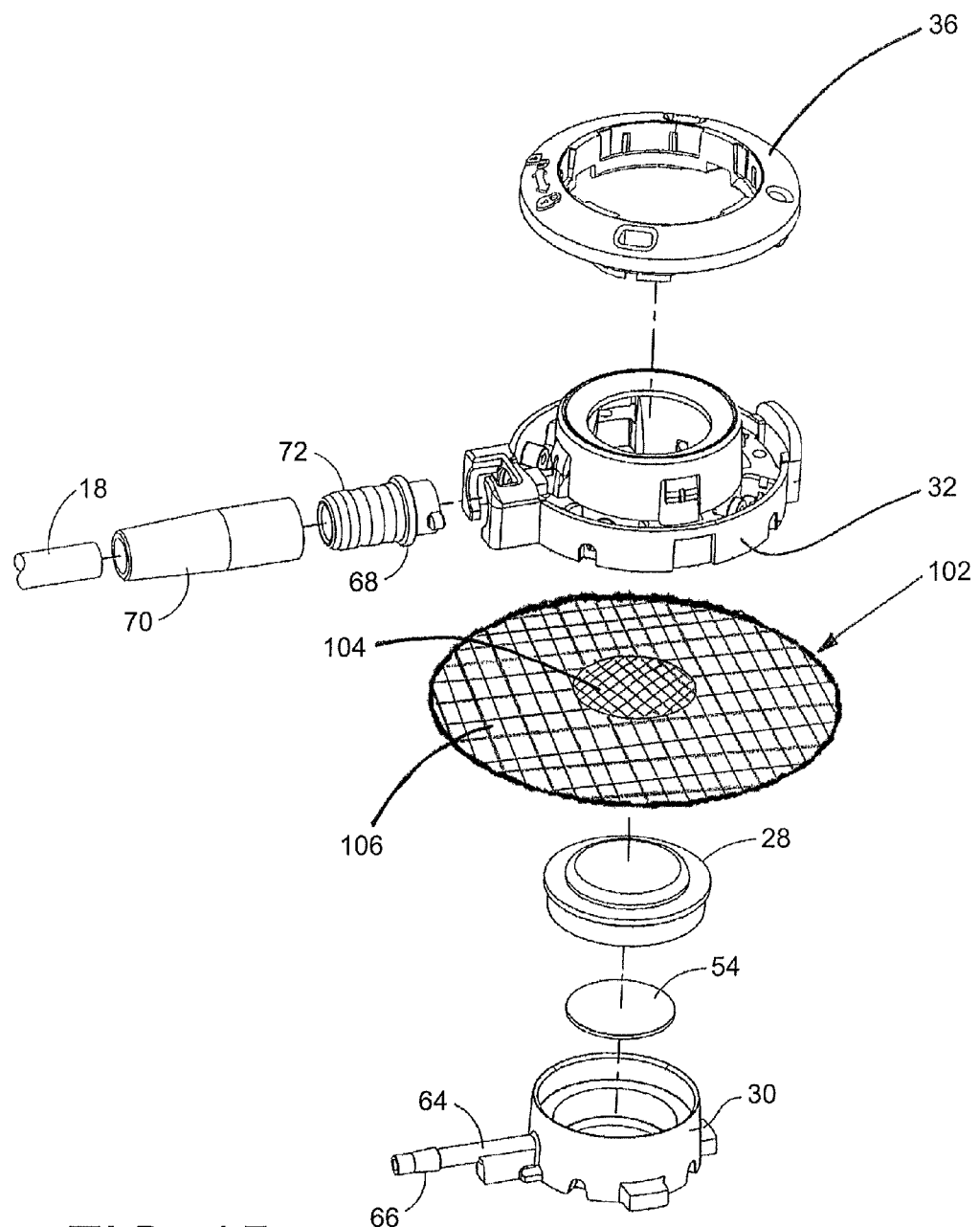
FIG. 15 depicts an exploded perspective view of another exemplary alternative injection port having a tissue in-growth promoting surface.
Figure 16:
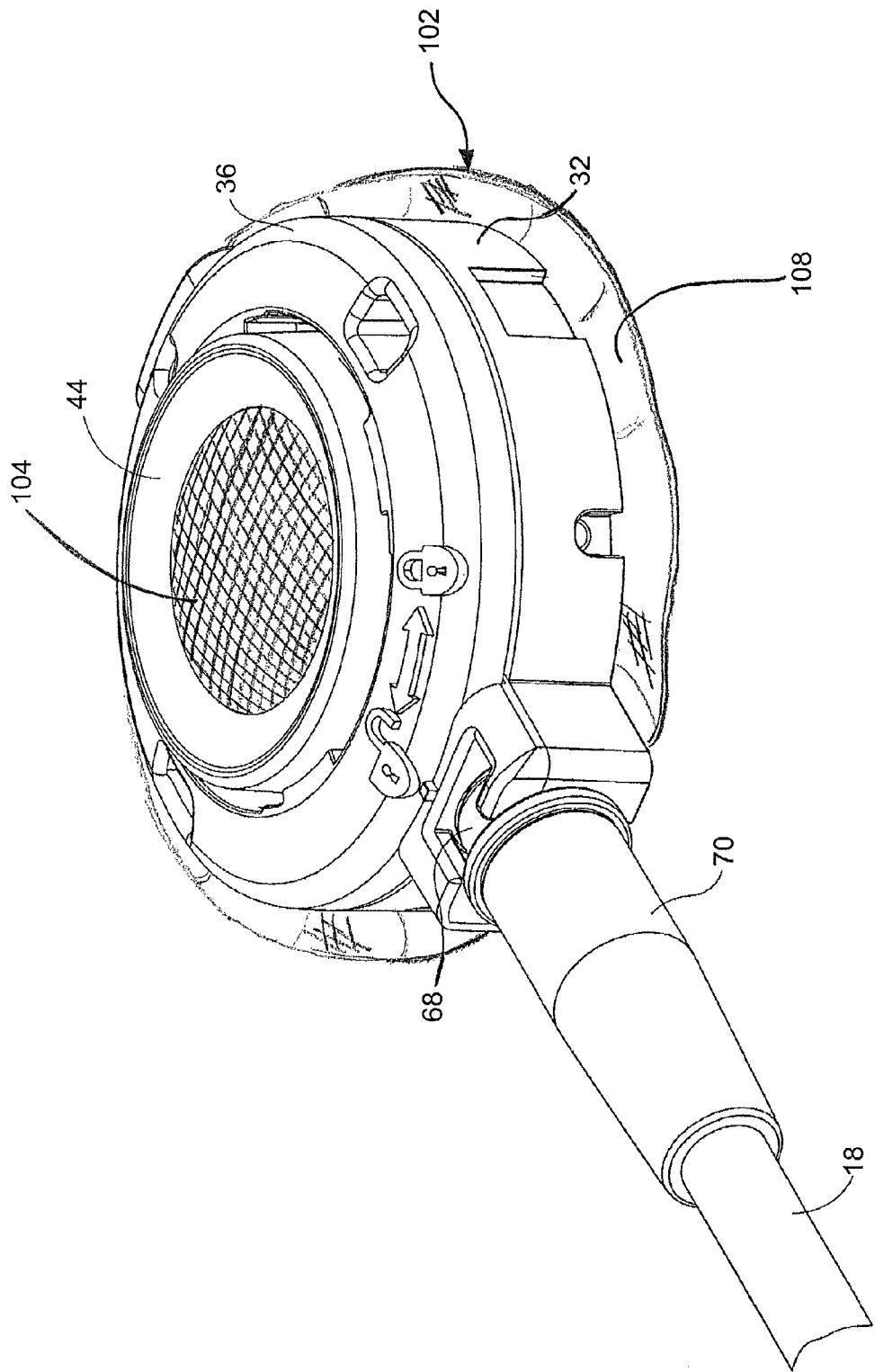
FIG. 16 depicts a perspective view of the injection port of FIG. 15, in assembled form.

In the example shown in FIGS. 15-16, a disc-shaped layer of mesh (102) is positioned between port base (30) and port body (32), directly above septum (28). When port base (30) is mounted within port body (32) in the manner described previously, mesh (102) will be trapped between port base (30) and port body (32) with a center portion (104) of mesh (102) overlying septum (28). As best seen in FIG. 16, mesh (102) is sized such that when trapped between port base (30) and port body (32), a portion (108) of mesh (102) extends outward of the injection port around the lower periphery of port body (32). When the injection port of FIGS. 15-16 is implanted in a patient, center portion (104) of mesh (102) as well as the portion (108) of mesh (102) extending outwardly away from the perimeter of port body (102) will be exposed such that tissue may grow into and around these exposed portions of mesh (102). Also, the exposed portion (108) of mesh (102) extending away from port body (32) may be used to further secure the port within a patient, such as by suturing or tacking exposed portion (108) to the fascia or other tissue in the patient.

As also shown in FIG. 15, mesh layer (102) is configured to have regions of varying density (in terms of weight, mesh size, and/or thickness). In the example shown, center portion (104) has a greater density than outer annular portion (106). Since center portion (104) overlies septum (28) when the injection port is assembled, the increased density of center portion (104) provides tactile feedback for locating septum (28) (by feel, through the patient's skin) and/or detecting that a needle has penetrated septum (28).

As an alternative to center portion (104) of mesh (102) having a greater density, outer annular portion (106) may be configured to have a greater density than center portion (104). This may be desirable in order to provide greater structural integrity in mesh (102) (e.g., to prevent tearing of mesh (102)), without inhibiting needle penetration through center portion (104). Center portion (104) of mesh (102) may even be eliminated entirely such that surgical mesh (102) forms an annulus. In this arrangement, septum (28), or at least a center portion thereof, will not be covered by mesh (102).

While mesh (102) in FIGS. 15-16 is positioned between port base (30) and port body (32) above septum (28), one or more surgical mesh layers may be mounted at least partially within other locations of the injection port. By way of example, a mesh layer similar to mesh (102) may be positioned between septum (28) and port base (30), and/or between port body (32) and actuator (36), with at least a portion of the mesh exposed in order to promote tissue growth into and around the mesh layer.

III. Tissue in-Growth Promoter Attachable to Injection Port

A. Sleeve Made from Tissue in-Growth Promoting Material

Figure 17:
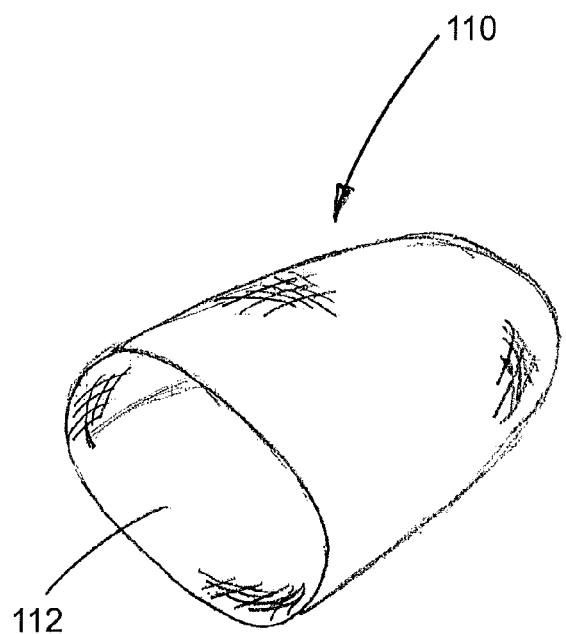
FIG. 17 depicts a perspective view of an exemplary tissue in-growth promoting sleeve for use with an injection port.

FIG. 17 depicts another merely illustrative example for promoting tissue in-growth in order to secure an injection port within a patient. In this example, a sleeve (or pouch) (110) made of a tissue in-growth promoting material is provided. Sleeve (110) is sized and configured such that injection port (28) may be inserted therein through open end (112). Sleeve (110) may be made of any of the variety of tissue in-growth promoting materials described previously, such as a surgical mesh. In the example shown, sleeve (110) comprises polypropylene mesh. The mesh used in forming sleeve (110) is of sufficient density to provide structural integrity while still allowing the injection port to be secured within a patient in any of the ways previously discussed (e.g., fasteners, sutures, etc.). If desired, sleeve (110) may have one or more apertures or other openings located to be positioned over features on the injection port that facilitate securing the port within a patient (e.g., apertures positionable over slots (80) on actuator (36) so as to allow the use of an applier to rotate the actuator and deploy fasteners (34), etc.).

After the injection port is inserted into sleeve (110), the sleeve (110) may be secured to the injection port in any of a variety of ways. For example, the open end (112) of sleeve (110) may be secured about sleeve (70) of injection port (28) and/or catheter (18) simply by tying a suture about open end (112). As another merely illustrative example, open end (112) may include a drawstring or similar feature. Alternatively, sleeve (110) may be secured to injection port (28) using a biocompatible adhesive, heat staking, vibration welding, ultrasonic welding, and other ways known in the art. In the present example, after injection port (28) is inserted into open end (112) of sleeve (110), sleeve (110) is heat shrunk about port (28).

If mesh sleeve (110) is sufficiently large, when injection port (28) with attached catheter (18) is inserted into sleeve (110) a portion of sleeve (70) or even catheter (18) may be located within mesh sleeve (110). In this manner, mesh sleeve (110) may also be secured to sleeve (70) and/or a portion of catheter (18). When implanted, tissue will grow into and around the portion of mesh sleeve (110) covering sleeve (70) and/or catheter (18), thereby reducing the likelihood of (if not preventing) catheter (18) becoming disconnected from injection port (28).

Sleeve (110) may further be configured to have one or more regions of varying density, similar to mesh layer (102) in FIG. 15. Thus, sleeve (110) may have a region of greater or lower density located so as to be positionable over septum (28) when injection port (26) is inserted into sleeve (110). As yet another alternative, sleeve (110) may include an aperture located so as to be positionable over septum (28) such that septum (28) remains fully exposed after injection port (26) is inserted into sleeve (110). Other suitable configurations for sleeve (110) will be apparent to those of ordinary skill in the art in view of the teachings herein.

B. Sheath Made from Tissue in-Growth Promoting Material

Figure 18:
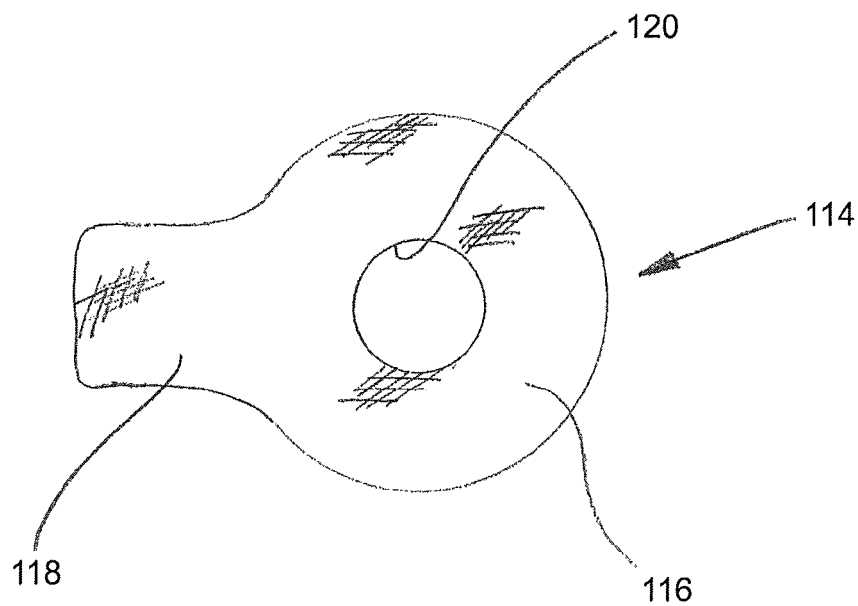
FIG. 18 depicts a top plan view of an exemplary tissue in-growth promoting sheath for use with an injection port.
Figure 19:
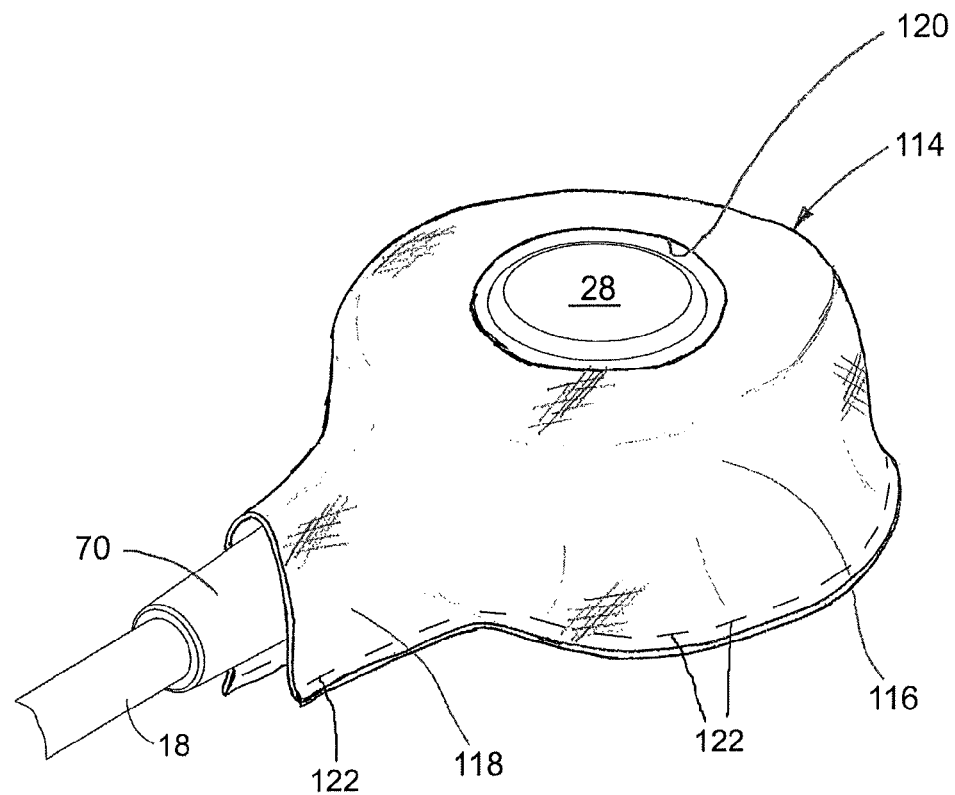
FIG. 19 depicts a perspective view of the sheath of FIG. 18 mounted over an injection port.

FIGS. 18-19 depict an example comprising a sheath (114) made of a tissue in-growth promoting material such as surgical mesh. Sheath (114) is configured to be draped over injection port (26), particularly after the injection port has been positioned or secured in a patient. Sheath (114) includes a first portion (116) configured to be draped over injection port (26), and a second portion (118) configured to be draped over a portion of catheter (18). In the example shown, first portion (116) has a generally circular shape corresponding to the shape of injection port (26). It should be kept in mind, however, that a variety of other shapes may be employed for first portion (116) of sheath (114).

First portion (116) also includes an aperture (120) configured and located such that, when first portion (116) is draped over injection port (26), septum (26) is exposed through aperture (120) (see FIG. 19). In some other versions, first portion (116) of sheath (114) may be configured similar to mesh disc (102) shown in FIG. 15 such that aperture (120) is replaced by a center portion of mesh having a different density than an outer annular portion.

Sheath (114) may be draped over injection port (28) before or after the injection port is positioned within a patient. If draped over injection port (28) before the port is positioned within a patient, sheath (114) may be secured to the injection port using, for example, an adhesive. Alternatively, injection port (28) may first be positioned within a patient, and the port even secured in place (e.g., using fasteners (34), etc.), before sheath (114) is draped over the injection port. Thereafter, sheath (114) may be secured in place over injection port (28), such as by sutures (122). Sutures (122) may be used to attach sheath (114) to tissue surrounding implanted port (28), as shown in FIG. 19. Of course any of a variety of other fasteners may be used in place of, or in addition to, sutures (122), such as surgical tacks, staples and the like.

Second portion (118) of sheath (114) extends radially away from first portion (116), and is configured to drape over a portion of catheter (18). In the example shown in FIG. 19, second portion (118) extends over a portion of sleeve (70) through which catheter (18) extends. It will be understood that second portion (118) may be configured so as to extend over not only sleeve (70) but also a portion of catheter (18) located distally of sleeve (70). Second portion (118) may be secured over or to catheter (18) and sleeve (70) by any of a variety of means, such as sutures (122).

When sheath (114) is positioned over injection port (28) within a patient, tissue surrounding the implantation site may grow into and around the mesh of sheath (114), helping to retain port (28) in its proper location. In addition, second portion (118) of sheath (114) may help substantially prevent catheter (18) from becoming disconnected from port (28). While second portion (118) may be omitted, second portion (118) may also help prevent inadvertent puncture of or other damage to catheter (18), particularly if sheath (114) or at least second portion (118) is made of a mesh or other material having sufficient strength and/or density.

C. Attachable Housing Having Tissue in-Growth Promoting Surface

As an alternative to providing tissue in-growth promoting surfaces on the injection port, or in addition thereto, one or more tissue in-growth promoting surfaces may be provided on a frame attachable to the injection port. Such an attachable frame may be configured to be attached to the injection port by the surgeon (e.g., as an adapter, etc.), thus allowing the surgeon to determine whether or not tissue in-growth promotion is desired. An injection port may even be supplied with multiple frames, each of which has different types, locations and or other characteristics of tissue in-growth promoting surfaces. For example, one frame when attached to the injection port may provide a tissue in-growth promoting surface beneath the injection port, while another frame may be configured to provide tissue in-growth promoting surfaces both beneath and around the periphery of the injection port when attached thereto. Such frames may be configured to be attached to the injection port in any of a variety of ways, such as snap-fit over a portion of the injection port and/or the use of various fasteners such as a hook and loop fastener arrangement. Merely illustrative examples of such frames will be described in greater detail below, while other suitable versions of such frames will be apparent to those of ordinary skill in the art in view of the teachings herein.

1. Frame Configured for Snap-Fit onto Injection Port

Figure 22:
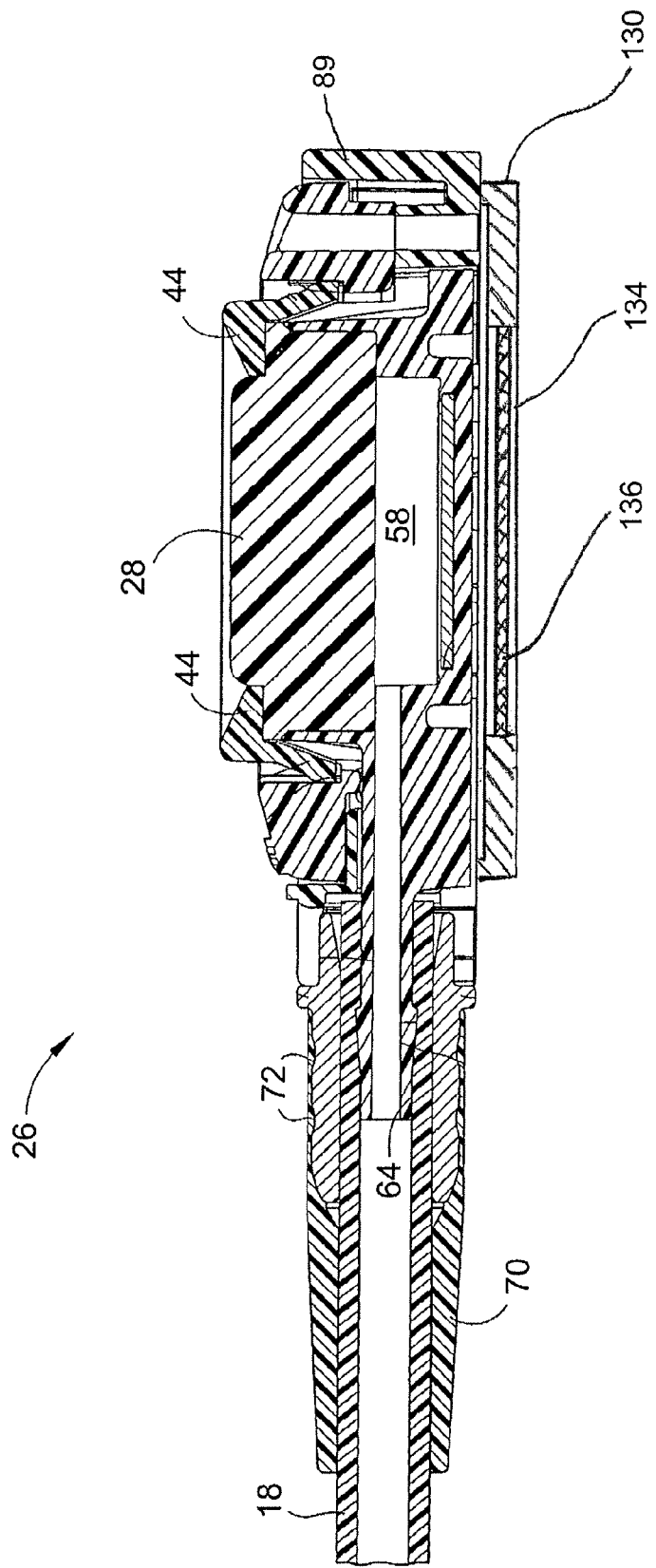
FIG. 22 depicts a side cross-sectional view of the frame of FIG. 20 attached to an injection port.

FIGS. 20-22 depict another example of a tissue in-growth promoting surface for use with an injection port. In this example, the tissue in-growth promoting surface is provided as part of a frame (130) configured to be attached to injection port (26). Frame (130) includes a bottom surface (132) having a central aperture (134) therein. In the example shown, the tissue in-growth promoting surface comprises a surgical mesh layer (e.g., polypropylene mesh, etc.) (136) positioned within central aperture (134). Mesh layer (136) may be secured within central aperture (134) in a variety of ways, such as by insert molding frame (130) around mesh layer (136). Alternatively, mesh layer (136) may even be secured over aperture (134) such as by affixing mesh layer (136) to the bottom surface (132) of frame (130) over central aperture (134). When frame (130) is attached to injection port (26), mesh layer (136) provides a tissue in-growth promoting surface on the underside of port (26). Of course frame (130) may be configured to provide one or more tissue in-growth promoting surfaces at a variety of other locations (e.g., about the outer sidewall of frame (130), etc.).

Frame (130) may be configured to be attached to injection port (26) in a variety of ways. By way of example, frame (130) may be attached to the injection port using a suitable adhesive. As yet another alternative, frame (130) and injection port (26) may be configured such that frame (130) may be attached to port (26) using a hook and loop fastener arrangement (e.g., hook members provided on a bottom surface of port (26) and mating hoops on a surface of frame (130)). In the example shown, frame (130) is configured to be snap fit over a portion of injection port (26). In particular, frame (130) includes a cylindrical chamber (138) located above mesh layer (136). Cylindrical chamber (138) includes a bottom surface (140) and an annular ledge (142) extending about bottom surface (140). When frame (130) is attached to injection port (26) as shown in FIG. 21, annular ledge (142) provides additional space between the bottom surface of port (26) and bottom surface (140) of frame (130) as well as mesh layer (136). This additional space allows for greater tissue in-growth between port (26) and frame (130), further securing injection port (26) within a patient.

Cylindrical chamber (138) is sized to receive port body (32) therein. A retention lip (144) is provided about the upper end of chamber (138), and is configured to retain port body (32) within chamber (138). A pair of cutouts (146, 148) are also provided in the outer wall of chamber (138) in order to accommodate extensions (88, 89) on port body (32). Cutouts (146, 148) also facilitate the attachment of frame (130) to port body (32) by allowing the upper end of frame (130) to be flexed outwardly. In this manner, frame (130) may be snap-fit over port body (32) with retention lip (144) pressed against an upper end surface of port body (32). A plurality of slots (156) are also provided in the bottom of frame (130). Slots (156) are configured and located to allow fasteners (34) to be deployed therethrough.

While frame (130) is configured to snap-fit over port body (32) such that mesh layer (136) is positioned adjacent the bottom of the injection port (26), the frame may have any of a variety of alternative configurations. For example, the frame may be configured to snap fit over the top of injection port (26) such that the mesh layer covers septum (28). Such an arrangement may be desirable in that the injection port (26) may first be secured within a patient (e.g., using fasteners (34)), and thereafter the mesh containing frame may be snap fit over the top of the injection port such that the surgical mesh layer covers septum (28) and/or is adjacent to septum (28). As with previously-described example, the mesh layer may be configured so as to not interfere with the insertion of a needle into septum (28), and may even be configured to provide tactile feedback. As yet another alternative, the frame may be configured to fit over the top and bottom of injection port (26)—e.g., a two part frame arranged similar to a clamshell. In such an arrangement, mesh layers may be provided beneath the injection port as well as over septum (28) or adjacent to septum (28).

In place of mesh layer (136), or in addition thereto, frame (130) may be configured similar to the previously described examples having one or more tissue in-growth promoting surfaces on the injection port. For example, portions of the bottom surface and/or outer peripheral sidewall of frame (130) may be textured in order to promote tissue in-growth. Such texturing may comprise, for example, one or more recesses, apertures, passageways, interconnected pores (i.e., a porous surface), ridges, protuberances (e.g., a roughened surface), trabeculae, or a combination of one or more of these features. In some versions, a plurality of recesses similar to recesses (100) in FIG. 14 may be provided on the bottom surface (132) and/or outer peripheral sidewall of frame (130). In addition, a surgical mesh or fabric may be secured over such recesses, similar to the example shown in FIG. 12.

As yet another merely illustrative alternative, frame (130) may have one or more tissue in-growth promoting materials such as surgical mesh bonded to the bottom surface (132) and/or outer peripheral sidewall of frame (130). Such tissue in-growth promoting material may, for example, take the form of a section of polypropylene mesh bonded to frame (130) so as to extend about the outer peripheral sidewall of frame (130) similar to the example shown in FIG. 5.

2. Ring-Shaped Frame Attachable to Injection Port

Figure 23:
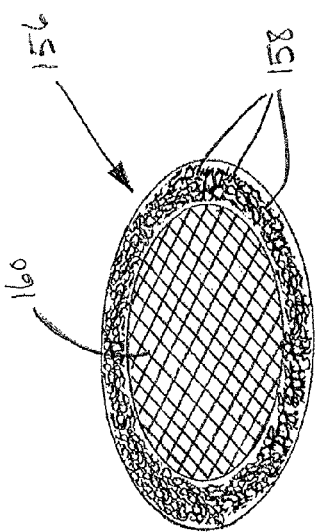
FIG. 23 depicts a perspective view of an exemplary alternative frame attachable to an injection port, with the frame including a tissue in-growth promoting surface.
Figure 24:
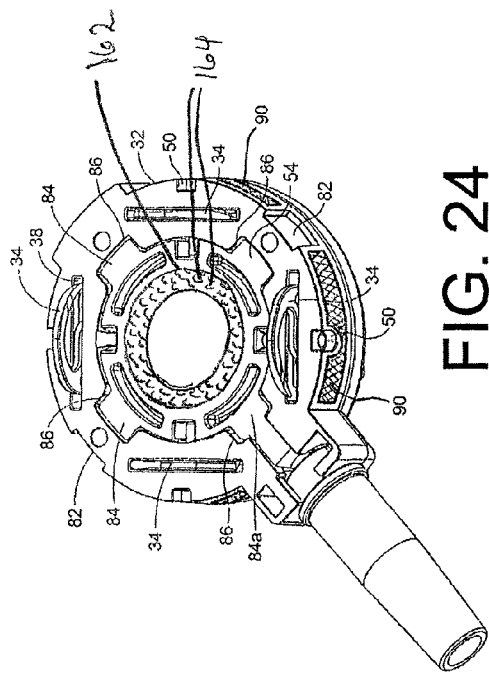
FIG. 24 depicts a perspective view of the bottom of an exemplary injection port configured for attachment of the frame of FIG. 23.
Figure 25:
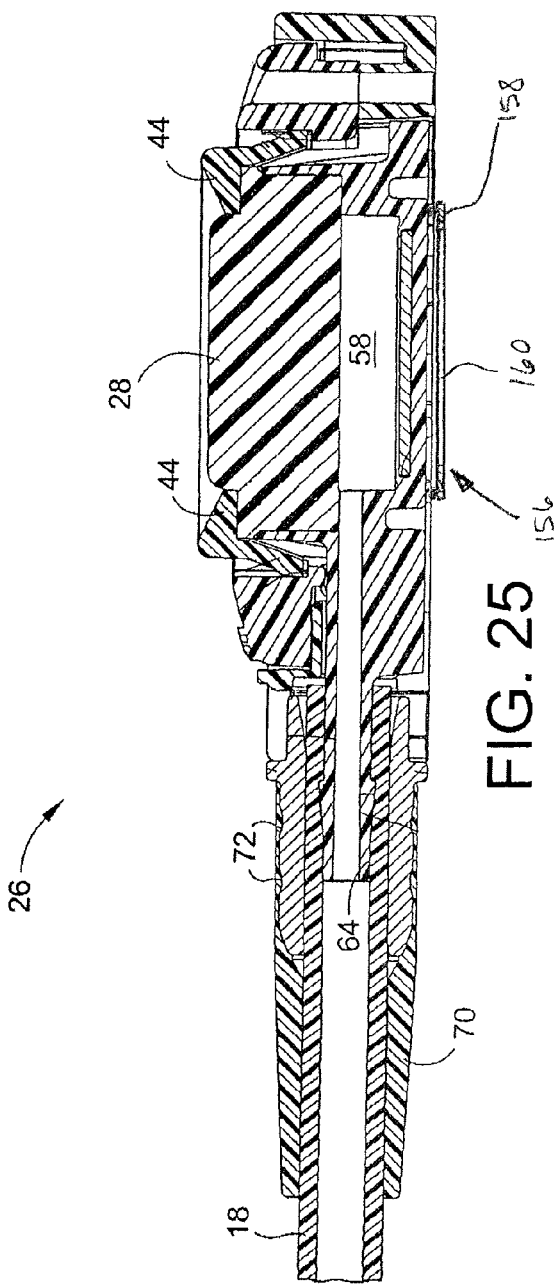
FIG. 25 depicts a side cross-sectional view of the frame of FIG. 23 attached to the injection port of FIG. 24.

FIGS. 23-25 depict another example of a frame attachable to an injection port, where the frame includes a tissue in-growth promoting material. In this example, the frame comprises a ring-shaped member (156) having a surgical mesh layer (160) (e.g., polypropylene mesh) mounted within the interior of ring-shaped frame (156). Frame (156) may be made from any of a variety of materials, such as plastic suitable for implantation in a patient (e.g., injection molded thermoplastic or thermoset polymer, rigid or semi-rigid, etc.). In the present example, frame (156) comprises a flexible fabric having a plurality of loops (158) on at least the upper surface of frame (156). Loops (158) are configured for securing frame (156) to an injection port having corresponding hook members on a surface thereof, thus providing a hook and loop fastening arrangement. It will be understood that loops (158) may be integrally formed with the fabric that forms frame (156); or loops (158) may be provided by a separate layer of material attached to frame (156).

As best seen in FIG. 24, the bottom surface of port base (30) includes a ring-shaped region (162) comprising a plurality of polymeric hooks (164) configured for attaching frame (156) to the bottom surface of port base (30). Since the hooks (164) extend away from the bottom surface of port base (30), when ring-shaped frame (156) is attached to the port (as shown in FIG. 25) mesh layer (160) is spaced away from the bottom surface of port base (30). Such spacing allows for additional tissue in-growth between mesh layer (160) and the bottom surface of port base (30). If desired, ring-shaped frame (156) also may be thicker than mesh layer (160) such that, when frame (156) is attached to the injection port, additional space is provided between mesh layer (160) and the bottom of the injection port to allow for even greater tissue in-growth.

It will be understood that the arrangement of the hook and loop fastener system may be reversed such that the loops are provided on port base (30) and the hooks are located on frame (156). Also, In addition, fastening systems or arrangements other than a conventional hook and loop fastener system may be used, such as mechanical fastening systems that allow frame (156) to be removably attached to port base (30) by pressing frame (156) against port base (30). By way of example, a fastening system employing interlocking mushroom-shaped stems sold under the name DUALLOCK™ by 3M may be employed. As yet another alternative, barb members may be provided on port base (30) in place of hooks or loops. Such barb members may engage frame (156) in order to retain frame (156) on port base (30). Such barb members may also be configured to penetrate the patient's fascia or other tissue at the implantation site in order to further retain the port in position. The barb members may even be made of a bio-absorbable material such that they are absorbed after sufficient tissue in-growth has occurred. As yet another merely illustrative alternative, frame members having one or more mesh layers may be provided for attachment to the injection port at various other locations (e.g., over septum (28) and/or adjacent to septum (28), etc.).

IV. Injection Port with Tissue in-Growth Promoting Feature Associated with Attached Catheter Previously-described examples promoted tissue in-growth about various regions or portions of an injection port in order to substantially prevent dislodgement or displacement, and/or limit the mobility of an injection port, such as an injection port of a gastric band system. In some instances it may be desirable to promote tissue growth around or along a catheter attached to an injection port and implanted within a patient in order to substantially prevent catheter disconnect and/or protect the catheter from damage (e.g., inadvertent needle puncture of the catheter when attempting to insert a needle into the septum of the injection port) or kinking, etc.

Any of the previously-described examples may be adapted to provide one or more tissue in-growth promoters on, along, adjacent or about a catheter attached to an injection port, with or without a tissue in-growth promoter also provided on or associated with the injection port itself. For example, a tissue in-growth promoting mesh may be integrally provided on at least a portion of the outer surface of the catheter and/or a connector used to attach the catheter to the injection port (e.g., connector (68) in FIG. 5) and/or a strain relief sleeve or similar structure used to protect or maintain attachment of the catheter (e.g., sleeve (70) in FIG. 5). Such mesh may be integrally provided on the catheter and/or connector using a bicompompatible adhesive, heat staking, vibration welding, ultrasonic welding, hot/cold upset, mechanical attachment, insert-molding, over-molding, and other ways known to those skilled in the art. Additional examples of ways in which tissue growth may be promoted around a catheter will be described in greater detail below, while other examples will be apparent to those of ordinary skill in the art in view of the teachings herein.

A. Surgical Mesh Wrapped Around Catheter

FIGS. 26-27 depict an exemplary tissue in-growth promoting surgical mesh structure (e.g., polypropylene, etc.) (170) having a first portion (172), a second portion (174) and a connector portion (176) that connects first portion (172) with second portion (174). It will be understood that connector portion (176) may be omitted, such that first portion (172) and second portion (174) are contiguous. First portion (172) of this example is configured similar to mesh disc (102) shown in FIGS. 15-16. Thus, first portion (172) of mesh (170) may be positioned between port base (30) and port body (32) directly above septum (28), such that first portion (172) will be trapped between port base (30) and port body (32), with a center portion (178) of first portion (172) overlying septum (28). As best seen in FIG. 27, first portion (172) is sized such that when trapped between port base (30) and port body (32), an outer annular portion (182) of first portion (172) extends outward of the injection port around the lower periphery of port body (32). When the injection port of FIG. 27 is implanted in a patient, center portion (178) of first portion (172) of mesh (170), as well as outer annular portion (182) will be exposed such that tissue may grow into and around these exposed portions of mesh (170). Also, the exposed annular portion (182) of mesh (170) extending away from port body (32) may be used to further secure the port within a patient such as by suturing or tacking exposed portion (182) to the fascia or other tissue in the patient.

Like the example shown in FIG. 15, first portion (172) of mesh (170) is configured to have regions of varying density (in terms of weight, mesh size, and/or thickness). In the example shown in FIGS. 26-27, center portion (178) has a greater density than the outer portion (180). Alternatively, outer portion (180) may be configured to have a greater density than center portion (178), as described previously. Center portion (178) of mesh (170) may even be eliminated entirely such that first portion (172) of surgical mesh (170) forms an annulus.

While first portion (172) of surgical mesh (170) is used to help secure injection port (26) within a patient (e.g., by tissue growth into the mesh), second portion (174) of surgical mesh (170) is configured to wrap around catheter (18) as shown. Second portion (174) is wrapped around catheter (18) in overlapping fashion, as shown in FIG. 27, and extends along a portion of the length catheter (18) beyond sleeve (70). Alternatively, second portion (174) of mesh (170) may be wrapped around catheter (18) in a spaced apart-fashion such that gaps are provided between adjacent revolutions of second portion (174). A portion of the distal end (184) of second portion (174) is tucked under the adjacent revolution of second portion (174) in order to secure second portion (174) wrapped around catheter (18). Alternatively, or in addition thereto, second portion (174) may be secured to at least a portion of catheter (18) using a suitable adhesive, or other means known to those skilled in the art.

When the injection port shown in FIG. 27 is implanted in a patient, first and second portions (172, 174) of surgical mesh (170) will allow for tissue growth into and around the mesh. Such tissue in-growth may not only help substantially maintain injection port (26) in place, but may also substantially prevent catheter (18) from becoming disconnected from the injection port. In addition, particularly if at least second portion (174) of mesh (170) is made from a sufficiently dense material, inadvertent puncture of catheter (18) may be substantially prevented. Furthermore, the strength of second portion (174) and/or the additional structural support provided by tissue growing in/around second portion (174) may substantially reduce the likelihood of catheter (18) kinking or tearing near port (26).

Second portion (174) of surgical mesh (170) may be provided in any of a variety of lengths and widths. In fact, second portion (174) may be sufficiently long so as to be wrapped around the entire length of catheter (18). In addition, second portion (174) may be wrapped around not only a portion of catheter (18), but also around extension (88) on port body (32) and/or additional portions of sleeve (70) in order to further prevent catheter disconnect.

In addition, second portion (174) of surgical mesh (170) may be used with any of the previously-described examples. For instance, an elongate strip of surgical mesh similar to second portion (174) may be attached to frame (130) in FIG.

20 or frame (156) in FIG. 23 so as to extend away from the frame (130, 156). When either of these frames (130, 156) is attached to an injection port in the manner previously described, the elongate strip of surgical mesh extending from the frame (130, 156) may be wrapped around the catheter similar to what is shown in FIG. 27. It is even contemplated that an elongate strip of surgical mesh similar to second portion (174) in FIG. 26 may simply be wrapped around the fluid conduit to promote tissue in-growth. If desired, one end of such an elongate strip may be attached to the injection port using, for example, an adhesive. In addition, the surgical mesh may be wrapped around at least a portion of the catheter where the catheter is attached to the injection port (e.g., around sleeve (70), etc.).

B. Pleated Surgical Mesh Associated with Catheter

FIGS. 28-29 depict another example of a tissue in-growth promoting surgical mesh (e.g., polypropylene, etc.) (190) that includes a catheter disconnect prevention portion. In this example, surgical mesh (190) has a first portion (192) configured for attachment to the bottom of injection port (26). First portion (192) may be configured similar to first portion (172) in FIG. 26, and may be trapped between components of the injection port such that a region of first portion (192) is exposed for tissue in-growth. In the example shown, however, first portion (192) comprises a disc-shaped member configured to be attached to the bottom surface of injection port (26) by using a suitable adhesive. Alternatively, first portion (192) may be attached to the bottom surface of port (26) using hook and loop fasteners, sutures, or any of a variety of other fastening means. As yet another alternative, first portion (192) may simply be positioned beneath injection port (26) in a patient such that when fasteners (34) are deployed to secure port (26) in place, first portion (192) of mesh (190) will be secured in place between port (26) and the patient's tissue by fasteners (34).

Also in the present example, first portion (192) of surgical mesh (190) is slightly larger than the bottom surface of injection port (26) such that an annular region (200) of first portion (192) extends beyond the outer periphery of port (26). This exposed annular region (200) not only provides an area for additional tissue in-growth, it may also be secured within a patient using sutures, staples, surgical tacks, or other fasteners.

Second portion (194) of surgical mesh (190) is connected to first portion (192) by connector portion (196), which is attached to a first end of second portion (194). Once again it will be understood that connector portion (196) may be omitted, such that first portion (192) and second portion (194) are contiguous. While second portion (194) comprises an elongate strip of mesh similar to second portion (174) in FIG. 26, second portion (194) of FIGS. 28-29 further includes a plurality of apertures (198) extending through the mesh along the length of second portion (194). In the embodiment shown, each aperture (198) is located centrally in the width direction of second portion (194), and apertures (198) are substantially evenly spaced along substantially the entire length of second portion (194). Of course, this is merely one exemplary configuration, as any of a variety of alternative arrangements of apertures (198) may be provided.

Second portion (194) of surgical mesh (190) is configured such that catheter (18) is threaded through each of apertures (198), resulting in the pleating of second portion (194), as shown in FIG. 29. Thus, catheter (18) extends through apertures (198) in adjacent pleats. By providing a pleated surgical mesh along at least a portion of the length of catheter (18), greater mesh surface area for tissue in-growth is provided. If desired, a suitable adhesive may be used to secure apertures (198) to the outer surface of catheter (18) or even sleeve (70) if desired.

Second portion (194) of surgical mesh (190) may be provided in any of a variety of lengths and widths. In fact, second portion (194) may be sufficiently long so as to extend along the entire length of catheter (18). In addition, second portion (194) may be provided about not only a portion of catheter (18), but also about extension (88) on port body (32) and/or additional portions of sleeve (70) in order to further prevent catheter disconnect.

In addition, second portion (194) of surgical mesh (190) may be used with any of the previously-described examples. For instance, an apertured elongate strip of surgical mesh similar to second portion (194) may be attached to frame (130) in FIG. 20 or frame (156) in FIG. 23 so as to extend away from the frame (130, 156). When either of these frames (130, 156) is attached to an injection port in the manner previously described, the catheter (18) may be threaded through the pleated strip of surgical mesh extending from the frame (130, 156) in a manner similar to that shown in FIG. 29. It is even contemplated that a pleated and apertured elongate strip of surgical mesh similar to second portion (194) in FIG. 28 may be use by itself to promote tissue in-growth around the fluid conduit of an implanted injection port. If desired, a first end of such a pleated strip may be attached to the injection port using, for example, an adhesive. In addition, the pleated surgical mesh may extend about at least a portion of the catheter where the catheter is attached to the injection port (e.g., adjacent sleeve (70), as shown in FIG. 29).

C. Frame Having Catheter Disconnect Prevention Portion

Figure 30:
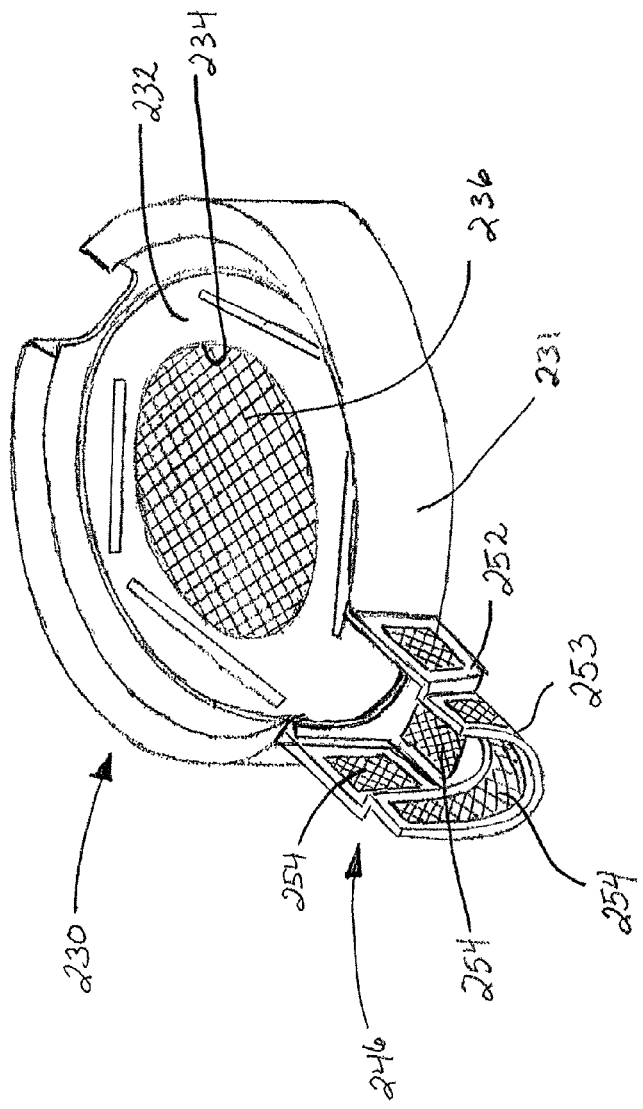
FIG. 30 depicts a perspective view of an exemplary alternative frame attachable to an injection port, with the frame including tissue in-growth promoting surfaces.

FIG. 30 depicts yet another example of an arrangement for providing a tissue in-growth promoter for preventing catheter disconnect. In this example, a catheter disconnect prevention portion comprising retention member (246) is provided on a frame (230) configured to be attached to injection port (26) described previously. Retention member (246) includes one or more mesh layers (254). Frame (230) is configured such that when attached to injection port (26), mesh layers (254) are located so as to provide a tissue in-growth promoting surface adjacent at least a portion of a catheter attached to injection port (26).

Frame (230) is configured similar to frame (130) described previously, and thus includes a bottom surface (232) having a central aperture (234) therein. A surgical mesh layer (e.g., polypropylene mesh, etc.) (236) is positioned within central aperture (234). It will be understood, however, that central aperture (234) and mesh layer (236) may be omitted from this example. Mesh layer (236) may be secured within central aperture (234) in a variety of ways, such as by insert molding frame (230) around mesh layer (236). When frame (230) is attached to injection port (26), mesh layer (236) provides a tissue in-growth promoting surface on the underside of port (26). Of course frame (230) may be configured to provide one or more tissue in-growth promoting surfaces at a variety of other locations (e.g., about the outer sidewall of frame (230), etc.).

Frame (230) may be configured to be attached to injection port (26) in a variety of ways. By way of example, frame (230) may be attached to the injection port using a suitable adhesive. As yet another alternative, frame (230) and injection port (26) may be configured such that frame (230) may be attached to port (26) using a hook and loop fastener arrangement (e.g., hook members provided on a bottom surface of port (26) and mating hoops on a surface of frame (230)). In the example shown, frame (230) is configured to be snap fit over a portion of injection port (26), in the manner described previously with respect to frame (130) shown in FIGS. 20-22.

Retention member (246) extends away from sidewall (231), which defines a cylindrical chamber portion of frame (230). Retention member (246) includes a first portion (252) and a second portion (253). Retention member (246) is further configured such that when frame (230) is attached to port (26), first portion (252) extends along and partially around extension (88) on port (26) and second portion (253) extends along and partially around sleeve (70). In this manner, retention member (246) extends along and partially around catheter (18) attached to port (26) (since catheter (18) extends through sleeve (70) and extension (88)), and mesh layers (254) provide tissue in-growth promoting surfaces for retaining catheter (18) to port (26).

While frame (230) is configured to snap-fit over port body (32) such that retention member (246) extends along and partially around extension (88) and sleeve (70) of port (26), the frame may have any of a variety of alternative configurations. For example, retention member (246) may be configured as a flat plate (or similar arrangement) that extends along the bottom surface of extension (88) and sleeve (70) rather than a generally U-shaped member as depicted. In addition, retention member (246) may include a single U-shaped portion rather than first and second portions configured to separately and matingly receive extension (88) and sleeve (70) of port (26). Also, mesh layers (254) may be provided on retention member (246) in any of the variety of ways previously described (e.g., insert molding about a mesh fabric or rigid plastic screen, etc.).

In place of mesh layers (254), or in addition thereto, frame (230) may be configured similar to the previously described examples having one or more tissue in-growth promoting surfaces on the injection port. For example, portions of the bottom surface and/or outer peripheral sidewall of retention member (246) may be textured in order to promote tissue in-growth. Such texturing may comprise, for example, one or more recesses, apertures, passageways, interconnected pores (i.e., a porous surface), ridges, protuberances (e.g., a roughened surface), trabeculae, or a combination of one or more of these features. In some versions, a plurality of recesses similar to recesses (100) in FIG. 14 may be provided on the bottom surface and/or outer peripheral sidewall of retention member (246). In addition, a surgical mesh or fabric may be secured over such recesses, similar to the example shown in FIG. 12. As yet another merely illustrative alternative, frame (230) may have one or more tissue in-growth promoting materials such as surgical mesh bonded to the bottom surface and/or outer peripheral sidewall of retention member (246) similar to the example shown in FIG. 5.

It will be understood that the examples shown and described herein are merely exemplary, and may be modified by those skilled in the art. For example, biocompatible adhesives may be applied to an injection port and/or tissue in-growth promoting surfaces in order to further secure the port and/or fluid conduit in place. In addition, antimicrobial coatings may be applied to the surgical mesh and/or other portions of an injection port or fluid conduit. It should also be understood that tissue in-growth promoting features as described herein may be incorporated into virtually any type of implanted device. The above described examples of gastric band systems are mere illustrations. The inventors' contemplation is not limited to components of gastric band systems. By way of example only, tissue in-growth promoting features as described herein may be incorporated into an implanted drug infusion port, chemotherapy port, or any other type of implantable port that is used to deliver something to a patient (e.g., an injection, treatment, medication, etc.), to help a physician locate the implanted port through palpation of the patient. Still other types of implanted devices that may incorporate tissue in-growth promoting features as described herein will be apparent to those of ordinary skill in the art in view of the teachings herein.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I/We claim:

1. A surgically implantable injection port, comprising:
   (a) a housing, wherein the housing comprises a top, a bottom, a side, a port body, and a port base, wherein the side comprises one or more side surfaces oriented circumferentially around the housing;
   (b) a fluid reservoir defined in part by the housing;
   (c) a needle penetrable septum having an outer surface, wherein the septum defines part of the fluid reservoir such that the reservoir is configured to receive part of a needle inserted through the outer surface of the septum, wherein the outer surface of the septum is unobstructed by the housing; and
   (d) a tissue in-growth promoting surface integrally provided on at least one exterior side surface of the housing, wherein the tissue in-growth promoting surface comprises:
      (i) a plurality of recesses integrated into the housing, the plurality of recesses forming a textured region for promoting tissue in-growth, wherein the plurality of recesses are rigid, wherein the plurality of recesses define a matrix grid, wherein each recess of the plurality of recesses comprises an interior surface offset inwardly from an exterior of the side surface of the housing, wherein each recess of the plurality of recesses shares a common border with at least one other recess of the plurality of recesses, wherein the interior surface of each recess comprises a plurality of apertures, passageways, interconnected pores, ridges, or protuberances, and (ii) a surgical mesh at least partially attached to the housing, wherein the surgical mesh completely covers the plurality of recesses and thereby defines a pocket between the surgical mesh and the interior surface of individual recesses, wherein the surgical mesh is mounted at least partially within the housing, wherein part of the surgical mesh extends over the outer surface of the septum, wherein a first portion of the surgical mesh has a different density than a second portion of the surgical mesh, wherein the first portion and the second portion of the surgical mesh are configured to provide a tactile response when penetrated with a needle, wherein the second portion of surgical mesh circumscribes the outer perimeter of the first portion of the surgical mesh, wherein the surgical mesh is mounted between the port body and the port base of the housing.

2. The injection port of claim 1, wherein the surgical mesh comprises a biocompatible material.

3. The injection port of claim 1, wherein a portion of the surgical mesh extends away from the housing about at least a portion of an outer perimeter of the housing.

4. The injection port of claim 1, further comprising:
(a) a gastric band having an inflatable member; and
(b) a catheter coupling the reservoir with the inflatable member, wherein the reservoir, the catheter, and the inflatable member together form a closed fluid circuit,
wherein a third surgical mesh portion connects to and extends radially from the second surgical mesh portion, wherein the third surgical mesh comprises a plurality of apertures, wherein the catheter extends through the plurality of apertures in such a way that the third surgical mesh portion is associated with the length of the catheter.

5. The injection port of claim 1, wherein the bottom of the fluid reservoir comprises of a plate between the plurality of recesses integrated into the port base of the housing and the fluid reservoir, wherein the plate is secured to the port base, wherein the plate is configured to prevent a needle from puncturing through the port base.

6. A surgically implantable injection port, comprising:
(a) a housing, wherein the housing comprises a base;
(b) a fluid reservoir defined in part by the housing, wherein an interior surface of the base defines a bottom of the fluid reservoir;
(c) a needle penetrable septum, wherein the septum defines part of the fluid reservoir such that the reservoir is configured to receive part of a needle inserted through the septum;
(d) a catheter attached to the housing in communication with the reservoir; and
(e) a frame, wherein the frame is attached to the port housing, wherein one or both of the housing or the frame comprise a tissue in-growth promoting surface located on a plane oriented perpendicular to the interior surface of the base, wherein the frame is snap fit over a portion of the housing, wherein the frame is attached to the bottom of the housing, and wherein the tissue in-growth promoting surface is formed at least in part by at least:
(i) a textured region, where the textured region is on an exterior surface of the base of the housing, wherein the textured region comprises a matrix grid defining a plurality of recesses, wherein each individual recess comprises an interior surface, and
(ii) a surgical mesh having antimicrobial properties, wherein the textured region is fully covered by the surgical mesh, wherein the surgical mesh extends along a plane oriented perpendicular to the interior surface of the base, wherein the frame is ring-shaped with the surgical mesh also extending across an open center of the frame,
wherein part of the textured region defines an aperture extending radially from the ring-shaped frame configured to sheath a portion of the catheter attached to the housing,
wherein the bottom of the fluid reservoir comprises of a plate between the tissue in-growth promoting surface and the fluid reservoir, wherein the plate is secured to the base, wherein the plate is configured to prevent a needle from puncturing the base.

\* \* \* \* \*